(12) United States Patent
Wang et al.

(10) Patent No.: US 10,864,039 B2
(45) Date of Patent: Dec. 15, 2020

(54) CAVITARY TISSUE ABLATION SYSTEM

(71) Applicant: Innoblative Designs, Inc., Chicago, IL (US)

(72) Inventors: Yearnchee C. Wang, Mill Creek, WA (US); Terence Chan, Diamond Bar, CA (US)

(73) Assignee: Innoblative Designs, Inc., Chicago, IL (US)

( * ) Notice: Subject to any disclaimer, the term of this patent is extended or adjusted under 35 U.S.C. 154(b) by 880 days.

(21) Appl. No.: 15/419,256

(22) Filed: Jan. 30, 2017

(65) Prior Publication Data

US 2017/0215951 A1 Aug. 3, 2017

Related U.S. Application Data

(60) Provisional application No. 62/290,108, filed on Feb. 2, 2016.

(51) Int. Cl.
*A61B 18/14* (2006.01)
*A61B 90/00* (2016.01)
(Continued)

(52) U.S. Cl.
CPC ...... *A61B 18/1477* (2013.01); *A61B 18/1206* (2013.01); *A61B 18/148* (2013.01);
(Continued)

(58) Field of Classification Search
CPC ..... A61B 18/12; A61B 18/1206; A61B 18/14; A61B 18/1445; A61B 18/1448;
(Continued)

(56) References Cited

U.S. PATENT DOCUMENTS

| 4,699,147 A | 10/1987 | Chilson et al. |
| 4,976,711 A | 12/1990 | Parins et al. |

(Continued)

FOREIGN PATENT DOCUMENTS

| CN | 2610858 Y | 4/2004 |
| CN | 104546124 A | 4/2015 |

(Continued)

OTHER PUBLICATIONS

Non-Final Office Action dated Aug. 11, 2017 for U.S. Appl. No. 15/337,334 (11 Pages).

(Continued)

*Primary Examiner* — Michael F Peffley
*Assistant Examiner* — Khadijeh A Vahdat
(74) *Attorney, Agent, or Firm* — Brown Rudnick LLP

(57) ABSTRACT

The invention is a system for monitoring and controlling tissue ablation. The system includes a controller configured to selectively control energy emission from an electrode array of an ablation device based on ablation feedback received during an ablation procedure with the ablation device. The controller is configured to receive feedback data from one or more sensors during the ablation procedure, the feedback data comprising one or more measurements associated with at least one of operation of the electrode array of the ablation device and tissue adjacent to the electrode array. The controller is further configured to generate an ablation pattern for controlling energy emission from the electrode array of the ablation device in response to the received feedback data.

12 Claims, 27 Drawing Sheets

(51) Int. Cl.
*A61B 18/12* (2006.01)
*A61B 17/00* (2006.01)
*A61B 18/00* (2006.01)

(52) U.S. Cl.
CPC .......... *A61B 18/1492* (2013.01); *A61B 90/04* (2016.02); *A61B 2017/00053* (2013.01); *A61B 2017/00057* (2013.01); *A61B 2018/0016* (2013.01); *A61B 2018/0072* (2013.01); *A61B 2018/00267* (2013.01); *A61B 2018/00333* (2013.01); *A61B 2018/00577* (2013.01); *A61B 2018/00648* (2013.01); *A61B 2018/00708* (2013.01); *A61B 2018/00726* (2013.01); *A61B 2018/00744* (2013.01); *A61B 2018/00761* (2013.01); *A61B 2018/00791* (2013.01); *A61B 2018/00827* (2013.01); *A61B 2018/00839* (2013.01); *A61B 2018/00875* (2013.01); *A61B 2018/00886* (2013.01); *A61B 2018/00988* (2013.01); *A61B 2018/124* (2013.01); *A61B 2018/144* (2013.01); *A61B 2018/1417* (2013.01); *A61B 2090/0436* (2016.02); *A61B 2218/002* (2013.01)

(58) Field of Classification Search
CPC .............. A61B 18/1477; A61B 18/148; A61B 18/1492; A61B 2018/0016; A61B 2018/00267; A61B 2018/00333; A61B 2018/00577; A61B 2018/00648; A61B 2018/00708; A61B 2018/0072; A61B 2018/00726; A61B 2018/00744; A61B 2018/00761; A61B 2018/00791; A61B 2018/00827; A61B 2018/00839; A61B 2018/00875; A61B 2018/00886; A61B 2018/00988; A61B 2018/124; A61B 2018/1417; A61B 2018/144; A61B 2017/00053; A61B 2017/00057; A61B 2090/0436; A61B 90/04; A61B 2218/002
See application file for complete search history.

(56) References Cited

U.S. PATENT DOCUMENTS

| | | |
|---|---|---|
| 4,979,948 A | 12/1990 | Geddes et al. |
| 5,045,056 A | 9/1991 | Behl |
| 5,100,423 A | 3/1992 | Fearnot |
| 5,117,828 A | 6/1992 | Metzger et al. |
| 5,334,193 A | 8/1994 | Nardella |
| 5,429,605 A | 7/1995 | Richling; Bernd et al. |
| 5,471,982 A | 12/1995 | Edwards et al. |
| 5,472,441 A | 12/1995 | Edwards et al. |
| 5,486,161 A | 1/1996 | Lax et al. |
| 5,536,267 A | 7/1996 | Edwards et al. |
| 5,562,720 A | 10/1996 | Stern et al. |
| 5,657,760 A | 8/1997 | Ying et al. |
| 5,672,153 A | 9/1997 | Lax et al. |
| 5,672,173 A | 9/1997 | Gough et al. |
| 5,672,174 A | 9/1997 | Gough et al. |
| 5,683,384 A | 11/1997 | Gough et al. |
| 5,713,942 A | 2/1998 | Stern et al. |
| 5,728,143 A | 3/1998 | Gough et al. |
| 5,772,590 A | 6/1998 | Webster, Jr. |
| 5,782,827 A | 7/1998 | Gough et al. |
| 5,827,276 A | 10/1998 | LeVeen et al. |
| 5,840,076 A | 11/1998 | Swanson et al. |
| 5,846,239 A | 12/1998 | Swanson et al. |
| 5,855,576 A | 1/1999 | LeVeen et al. |
| 5,863,290 A | 1/1999 | Gough et al. |
| 5,868,736 A | 2/1999 | Swanson et al. |
| 5,868,776 A | 2/1999 | Wright |
| 5,871,483 A | 2/1999 | Jackson et al. |
| 5,888,198 A | 3/1999 | Eggers et al. |
| 5,891,136 A | 4/1999 | McGee et al. |
| 5,893,847 A | 4/1999 | Kordis |
| 5,913,855 A | 6/1999 | Gough et al. |
| 5,928,229 A | 7/1999 | Gough et al. |
| 5,935,123 A | 8/1999 | Edwards et al. |
| 5,961,513 A | 10/1999 | Swanson et al. |
| 5,980,517 A | 11/1999 | Gough |
| 6,009,877 A | 1/2000 | Edwards |
| 6,032,077 A | 2/2000 | Pomeranz |
| 6,036,689 A | 3/2000 | Tu et al. |
| 6,053,913 A | 4/2000 | Tu et al. |
| 6,053,937 A | 4/2000 | Edwards et al. |
| 6,063,081 A | 5/2000 | Mulier et al. |
| 6,071,278 A | 6/2000 | Panescu et al. |
| 6,071,280 A | 6/2000 | Edwards et al. |
| 6,099,526 A | 8/2000 | Whayne et al. |
| 6,112,123 A | 8/2000 | Kelleher et al. |
| 6,123,718 A | 9/2000 | Tu et al. |
| 6,142,993 A | 11/2000 | Whayne et al. |
| 6,221,071 B1 | 4/2001 | Sherry et al. |
| 6,241,666 B1 | 6/2001 | Pomeranz et al. |
| 6,251,109 B1 | 6/2001 | Hassett et al. |
| 6,258,087 B1 | 7/2001 | Edwards et al. |
| 6,309,352 B1 | 10/2001 | Oraevsky et al. |
| 6,312,408 B1 | 11/2001 | Eggers et al. |
| 6,312,429 B1 | 11/2001 | Burbank et al. |
| 6,358,248 B1 | 3/2002 | Mulier et al. |
| 6,379,353 B1 | 4/2002 | Nichols |
| 6,409,722 B1 | 6/2002 | Hoey et al. |
| 6,425,877 B1 | 7/2002 | Edwards |
| 6,454,766 B1 | 9/2002 | Swanson et al. |
| 6,491,710 B2 | 12/2002 | Satake |
| 6,494,902 B2 | 12/2002 | Hoey et al. |
| 6,503,247 B2 | 1/2003 | Swartz et al. |
| 6,522,930 B1 | 2/2003 | Schaer et al. |
| 6,537,248 B2 | 3/2003 | Mulier et al. |
| 6,537,272 B2 | 3/2003 | Christopherson et al. |
| 6,544,262 B2 | 4/2003 | Fleischman |
| 6,551,310 B1 | 4/2003 | Ganz et al. |
| 6,585,732 B2 | 7/2003 | Mulier et al. |
| 6,623,481 B1 | 9/2003 | Garbagnati et al. |
| 6,638,275 B1 | 10/2003 | McGaffigan et al. |
| 6,648,883 B2 | 11/2003 | Francischelli et al. |
| 6,663,622 B1 | 12/2003 | Foley et al. |
| 6,692,466 B1 | 2/2004 | Chow et al. |
| 6,736,810 B2 | 5/2004 | Hoey et al. |
| 6,736,811 B2 | 5/2004 | Panescu et al. |
| 6,743,226 B2 | 6/2004 | Cosman et al. |
| 6,764,487 B2 | 7/2004 | Mulier et al. |
| 6,770,072 B1 | 8/2004 | Truckai et al. |
| 6,780,183 B2 | 8/2004 | Jimenez, Jr. et al. |
| 6,805,131 B2 | 10/2004 | Kordis |
| 6,826,421 B1 | 11/2004 | Beatty et al. |
| 6,849,073 B2 | 2/2005 | Hoey et al. |
| 6,872,206 B2 | 3/2005 | Edwards et al. |
| 6,878,149 B2 | 4/2005 | Gatto |
| 6,955,641 B2 | 10/2005 | Lubock |
| 6,978,788 B2 | 12/2005 | Klimberg et al. |
| 6,984,232 B2 | 1/2006 | Vanney et al. |
| 7,104,989 B2 | 9/2006 | Skarda |
| 7,150,745 B2 | 12/2006 | Stern et al. |
| 7,156,845 B2 | 1/2007 | Mulier et al. |
| 7,169,144 B2 | 1/2007 | Hoey et al. |
| 7,247,155 B2 | 7/2007 | Hoey et al. |
| 7,276,061 B2 | 10/2007 | Schaer et al. |
| 7,306,593 B2 | 12/2007 | Keidar et al. |
| 7,326,208 B2 | 2/2008 | Vanney et al. |
| 7,344,535 B2 | 3/2008 | Stern et al. |
| 7,364,579 B2 | 4/2008 | Mulier et al. |
| 7,367,972 B2 | 5/2008 | Francischelli et al. |
| 7,371,231 B2 | 5/2008 | Rioux et al. |
| 7,399,299 B2 | 7/2008 | Daniel et al. |
| 7,416,552 B2 | 8/2008 | Paul et al. |
| 7,419,489 B2 | 9/2008 | Vanney et al. |
| 7,556,628 B2 | 7/2009 | Utley et al. |
| 7,632,268 B2 | 12/2009 | Edwards et al. |
| 7,717,909 B2 | 5/2010 | Strul et al. |
| 7,769,432 B2 | 8/2010 | Klimberg et al. |
| 7,776,034 B2 | 8/2010 | Kampa |

(56) References Cited

U.S. PATENT DOCUMENTS

| | | |
|---|---|---|
| 7,828,793 B2 | 11/2010 | Thompson et al. |
| 7,862,498 B2 | 1/2011 | Nguyen et al. |
| 7,879,030 B2 | 2/2011 | Paul et al. |
| 7,942,873 B2 | 5/2011 | Kwan et al. |
| 7,959,628 B2 | 6/2011 | Schaer et al. |
| 7,959,631 B2 | 6/2011 | DiCarlo |
| 8,034,022 B2 | 10/2011 | Boatman |
| 8,043,289 B2 | 10/2011 | Behl et al. |
| 8,048,069 B2 | 11/2011 | Skwarek et al. |
| 8,114,071 B2 | 2/2012 | Woloszko et al. |
| 8,224,416 B2 | 7/2012 | de la Rama et al. |
| 8,303,584 B2 | 11/2012 | Burdio Pinilla et al. |
| 8,388,573 B1 | 3/2013 | Cox |
| 8,398,624 B2 | 3/2013 | Rioux et al. |
| 8,409,193 B2 | 4/2013 | Young et al. |
| 8,444,638 B2 | 5/2013 | Woloszko et al. |
| 8,465,484 B2 | 6/2013 | Davalos et al. |
| 8,465,486 B2 | 6/2013 | Danek et al. |
| 8,588,886 B2 | 11/2013 | de la Rama et al. |
| 8,591,461 B2 | 11/2013 | Boatman |
| 8,617,158 B2 | 12/2013 | Garabedian et al. |
| 8,647,339 B2 | 2/2014 | Satake |
| 8,657,814 B2 | 2/2014 | Werneth et al. |
| 8,734,439 B2 | 5/2014 | Gough et al. |
| 8,814,855 B2 | 8/2014 | DiCarlo et al. |
| 8,834,461 B2 | 9/2014 | Werneth et al. |
| 8,979,838 B2 | 3/2015 | Woloszko et al. |
| 8,979,841 B2 | 3/2015 | Kunis et al. |
| 9,078,665 B2 | 7/2015 | Moss et al. |
| 9,131,980 B2 | 9/2015 | Bloom |
| 9,839,472 B2 | 12/2017 | Rioux et al. |
| 9,848,936 B2 | 12/2017 | Rioux et al. |
| 9,855,098 B2 | 1/2018 | Rioux |
| 2001/0031941 A1 | 10/2001 | Edwards et al. |
| 2002/0026186 A1 | 2/2002 | Woloszko et al. |
| 2002/0062123 A1 | 5/2002 | McClurken et al. |
| 2002/0087208 A1 | 7/2002 | Koblish et al. |
| 2002/0095152 A1 | 7/2002 | Ciarrocca et al. |
| 2002/0115992 A1 | 8/2002 | Utley et al. |
| 2002/0120259 A1 | 8/2002 | Lettice et al. |
| 2002/0120267 A1 | 8/2002 | Phan |
| 2002/0128641 A1 | 9/2002 | Underwood et al. |
| 2003/0009166 A1 | 1/2003 | Moutafis et al. |
| 2003/0036680 A1 | 2/2003 | Black |
| 2003/0130711 A1 | 7/2003 | Pearson et al. |
| 2003/0216725 A1 | 11/2003 | Woloszko et al. |
| 2003/0225403 A1 | 12/2003 | Woloszko et al. |
| 2004/0087936 A1 | 5/2004 | Stern et al. |
| 2004/0092960 A1 | 5/2004 | Abrams et al. |
| 2005/0049454 A1 | 3/2005 | Ouchi |
| 2005/0070894 A1 | 3/2005 | McClurken |
| 2005/0154386 A1 | 7/2005 | West et al. |
| 2006/0212032 A1 | 9/2006 | Daniel et al. |
| 2006/0259027 A1 | 11/2006 | Kwan et al. |
| 2007/0083195 A1 | 4/2007 | Werneth et al. |
| 2008/0004534 A1 | 1/2008 | Gelbart et al. |
| 2008/0015565 A1 | 1/2008 | Davison |
| 2008/0103494 A1 | 5/2008 | Rioux et al. |
| 2008/0140001 A1 | 6/2008 | Globerman et al. |
| 2009/0171340 A1 | 7/2009 | Young |
| 2009/0248021 A1 | 10/2009 | McKenna |
| 2009/0292177 A1 | 11/2009 | Eggers et al. |
| 2009/0299355 A1 | 12/2009 | Bencini et al. |
| 2010/0114087 A1 | 5/2010 | Edwards et al. |
| 2010/0256629 A1 | 10/2010 | Wylie et al. |
| 2010/0292689 A1 | 11/2010 | Davison et al. |
| 2011/0172485 A1 | 7/2011 | Lubock |
| 2011/0257646 A1 | 10/2011 | Utley et al. |
| 2012/0029510 A1 | 2/2012 | Haverkost |
| 2012/0059437 A1 | 3/2012 | Shalev |
| 2012/0109250 A1 | 5/2012 | Cates et al. |
| 2012/0172680 A1 | 7/2012 | Gelfand et al. |
| 2013/0085493 A1 | 4/2013 | Bloom et al. |
| 2013/0158536 A1 | 6/2013 | Bloom |
| 2013/0172870 A1 | 7/2013 | Germain et al. |
| 2013/0184702 A1 | 7/2013 | Neal, II et al. |
| 2013/0184706 A1 | 7/2013 | Gelbart et al. |
| 2013/0253506 A1 | 9/2013 | Rioux et al. |
| 2013/0310833 A1 | 11/2013 | Brown et al. |
| 2013/0338662 A1 | 12/2013 | Weber |
| 2014/0018788 A1 | 1/2014 | Engelman et al. |
| 2014/0018794 A1 | 1/2014 | Anderson et al. |
| 2014/0031810 A1 | 1/2014 | Mahvi et al. |
| 2014/0058376 A1 | 2/2014 | Horn et al. |
| 2014/0221998 A1 | 8/2014 | Latterell |
| 2014/0276731 A1 | 9/2014 | Voegele et al. |
| 2014/0276748 A1 | 9/2014 | Ku et al. |
| 2014/0378960 A1 | 12/2014 | Fischer et al. |
| 2015/0018817 A1 | 1/2015 | Willard |
| 2015/0141982 A1 | 5/2015 | Lee |
| 2016/0113707 A1 | 4/2016 | Sahakian et al. |
| 2016/0113708 A1 | 4/2016 | Moss et al. |
| 2016/0184008 A1 | 6/2016 | Papaioannou et al. |
| 2016/0317221 A1 | 11/2016 | Rioux |
| 2017/0000559 A1 | 1/2017 | Rioux et al. |
| 2017/0027633 A1 | 2/2017 | Wham et al. |
| 2017/0119454 A1 | 5/2017 | Rioux et al. |
| 2017/0172646 A1 | 6/2017 | Patel et al. |
| 2017/0215947 A1 | 8/2017 | Rioux et al. |
| 2017/0215951 A1 | 8/2017 | Wang et al. |
| 2017/0252092 A1 | 9/2017 | Rioux et al. |
| 2017/0281267 A1 | 10/2017 | Rioux et al. |
| 2017/0281271 A1 | 10/2017 | Rioux |
| 2018/0014880 A1 | 1/2018 | Rioux et al. |
| 2018/0078305 A1 | 3/2018 | Rioux et al. |
| 2018/0104004 A1 | 4/2018 | Rioux et al. |

FOREIGN PATENT DOCUMENTS

| | | |
|---|---|---|
| DE | 102010032932 A1 | 2/2012 |
| EP | 0777445 B1 | 6/1999 |
| EP | 2942023 A3 | 2/2016 |
| EP | 3040043 B1 | 1/2018 |
| JP | 3009735 B2 | 2/2000 |
| WO | 9510326 A1 | 4/1995 |
| WO | 9942047 A1 | 8/1999 |
| WO | 0051683 A1 | 9/2000 |
| WO | 2007103986 A2 | 9/2007 |
| WO | 2011143468 A2 | 11/2011 |
| WO | 2012015722 A1 | 2/2012 |
| WO | 2012050637 A1 | 4/2012 |
| WO | 2014022379 A1 | 2/2014 |
| WO | 2014189887 A2 | 11/2014 |
| WO | 2015/142674 A1 | 9/2015 |
| WO | 2015163846 A1 | 10/2015 |
| WO | 2015200518 A1 | 12/2015 |
| WO | 2016181318 A1 | 11/2016 |

OTHER PUBLICATIONS

Response to Non-Final Office Action Filed Sep. 20, 2017 for U.S. Appl. No. 15/337,334 (6 Pages).

Non-Final Office Action dated Aug. 11, 2017 for U.S. Appl. No. 15/624,327 (11 Pages).

Response to Non-Final Office Action Filed Sep. 19, 2017 for U.S. Appl. No. 15/624,327 (8 Pages).

Non-Final Office Action dated Aug. 4, 2017 for U.S. Appl. No. 15/624,230 (18 Pages).

Response to Non-Final Office Action Filed Sep. 20, 2017 for U.S. Appl. No. 15/624,230 (10 Pages).

"Aquamantys System" Product Brochure, Medtronic, 2014 (12 Pages).

"Starburst Talon" Specifications Brochure, Angiodynamics, 2013 (2 Pages).

Medtronic, "Aquamantys Bipolar Sealers." Electrosurgical Products, Jun. 2017. Retrieved Jul. 21, 2017. <http://www.medtronic.com/us-en/healthcare-professionals/products/general-surgery/electrosurgical/aquamantys-bipolar-sealers.html> (11 Pages).

International Search Report and Written Opinion dated Jun. 6, 2018 for International Application No. PCT/US2018/019151 (17 Pages).

(56) References Cited

OTHER PUBLICATIONS

International Search Report and Written Opinion of the International Searching Authority dated Sep. 16, 2018 for International Application No. PCT/US2018/036268 (11 Pages).
International Search Report and Written Opinion of the International Searching Authority dated Jun. 11, 2017 for International Application No. PCT/US2017/019398 (27 Pages).
Notice of Allowance dated Jul. 24, 2018 for U.S. Appl. No. 15/784,778 (12 Pages).
International Search Report and Written Opinion of the Interational Searching Authority dated Feb. 27, 2018 for International Application No. PCT/US2017/056754 (11 Pages).
Extended European Search Report dated Nov. 27, 2018 for European Application No. 16787228.2, (6 pages).
Extended European Search Report dated Jun. 12, 2019, for European Application No. 16860886.7, (8 pages).
Extended European Search Report dated Jul. 16, 2019 for European Application No. 17747970.6 (6 pages).
Official Action dated Jun. 19, 2019 for Japanese Patent Application No. 2018-540040 (11 pages).
Non-Final Office Action dated May 7, 2018 for U.S. Appl. No. 15/142,616 (13 Pages).
International Search Report and Written Opinion of the International Searching Authority dated Aug. 22, 2016 for International Application No. PCT/US2016/030081 (11 Pages).
International Search Report and Written Opinion of the International Searching Authority dated Aug. 5, 2015 for International Application No. PCT/US2015/020596 (13 Pages).
International Search Report and Written Opinion of the International Searching Authority dated Feb. 2, 2017 for International Application No. PCT/US2016/059345 (10 Pages).
International Search Report and Written Opinion of the International Searching Authority dated May 16, 2017 for International Application No. PCT/US2017/015582 (11 pages).
International Search Report and Written Opinion of the International Searching Authority dated May 16, 2017 for International Application No. PCT/US2017/015584 (11 pages).
International Search Report and Written Opinion of the International Searching Authority dated Nov. 29, 2013 or International Application No. PCT/US2013/052703 (11 Pages).
International Search Report and Written Opinion of the International Searching Authority dated Oct. 19, 2017 for International Application No. PCT/US2017/041501 (63 Pages).
Extended European Search Report dated Jun. 10, 2016 for European Application No. 13825361.2 (13 Pages).
International Search Report and Written Opinion of the International Searching Authority, dated Feb. 2, 2017 for International Application No. PCT/US2016/059345.
Extended European Search Report issued in European Application No. 17828289.3, dated Feb. 6, 2020, 5 pages.
Extended European Search Report issued in European Application No. 17895158.8, dated Feb. 28, 2020, 8 pages.
Extended European Search Report issued in European Application No. 19219030.4, dated Jun. 26, 2020, 6 pages.
International Search Report and Written Opinion of the International Searching Authority dated Aug. 26, 2018 for International Application No. PCT/US2017/059850 (10 Pages).
International Search Report and Written Opinion of the International Searching Authority dated Nov. 1, 2018 for International Application No. PCT/US2018/043654 (10 Pages).
International Search Report and Written Opinion of the International Searching Authority dated Nov. 15, 2018 for International Application PCT/US2018/043658 (15 Pages).

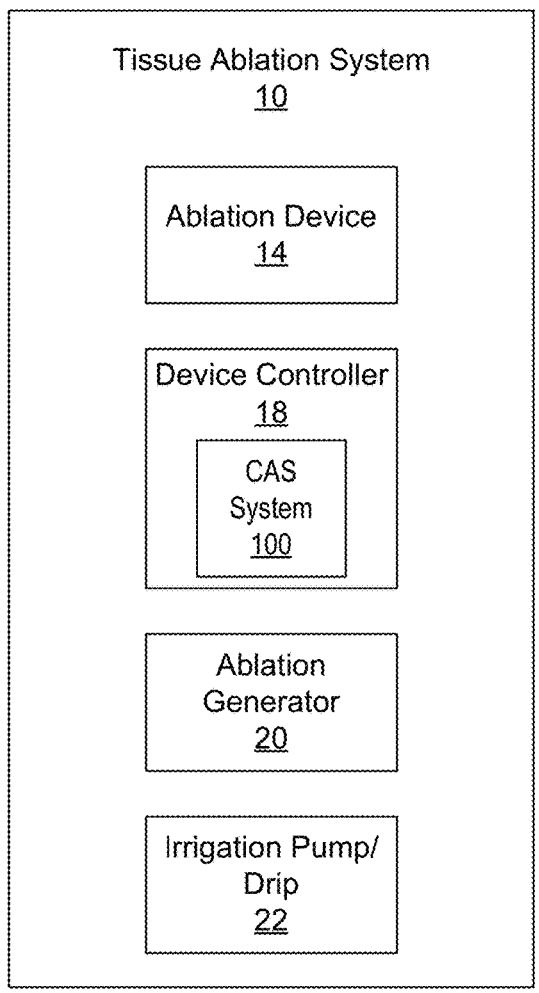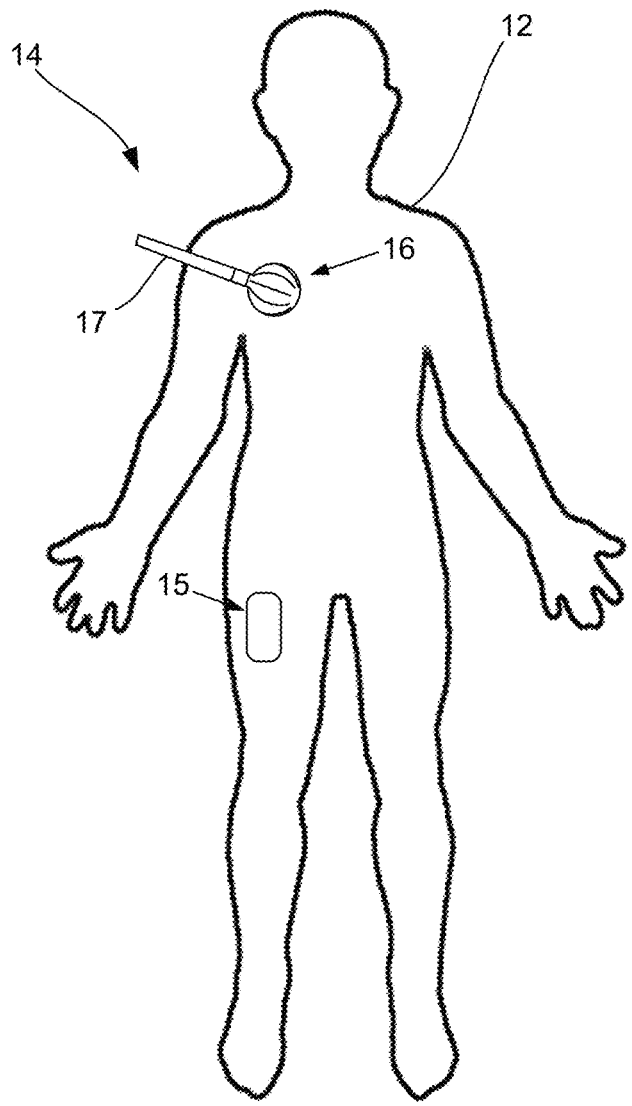
FIG. 1

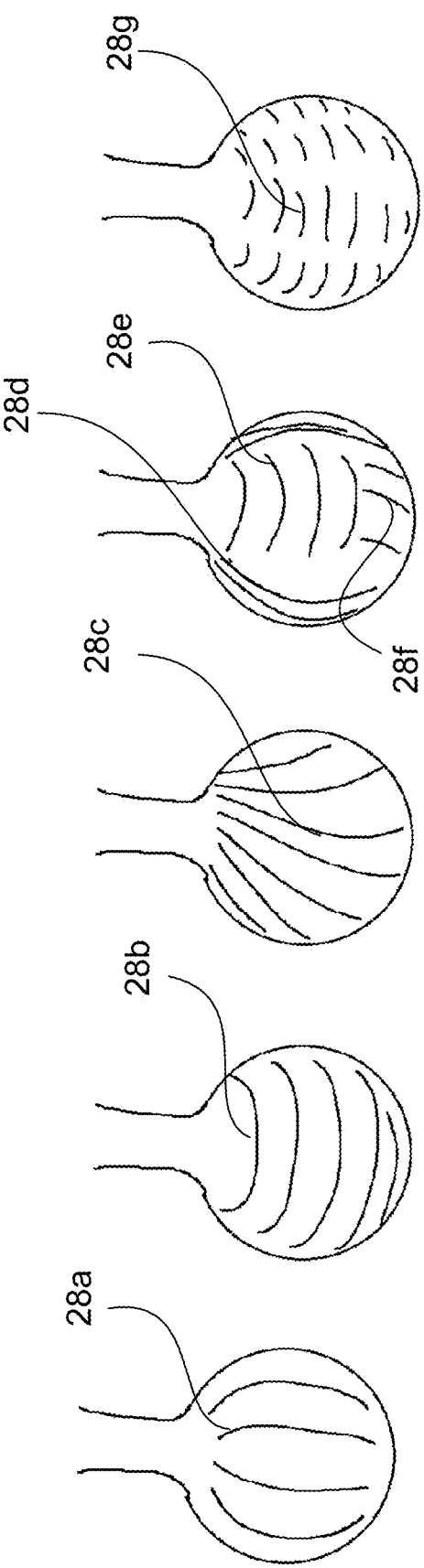

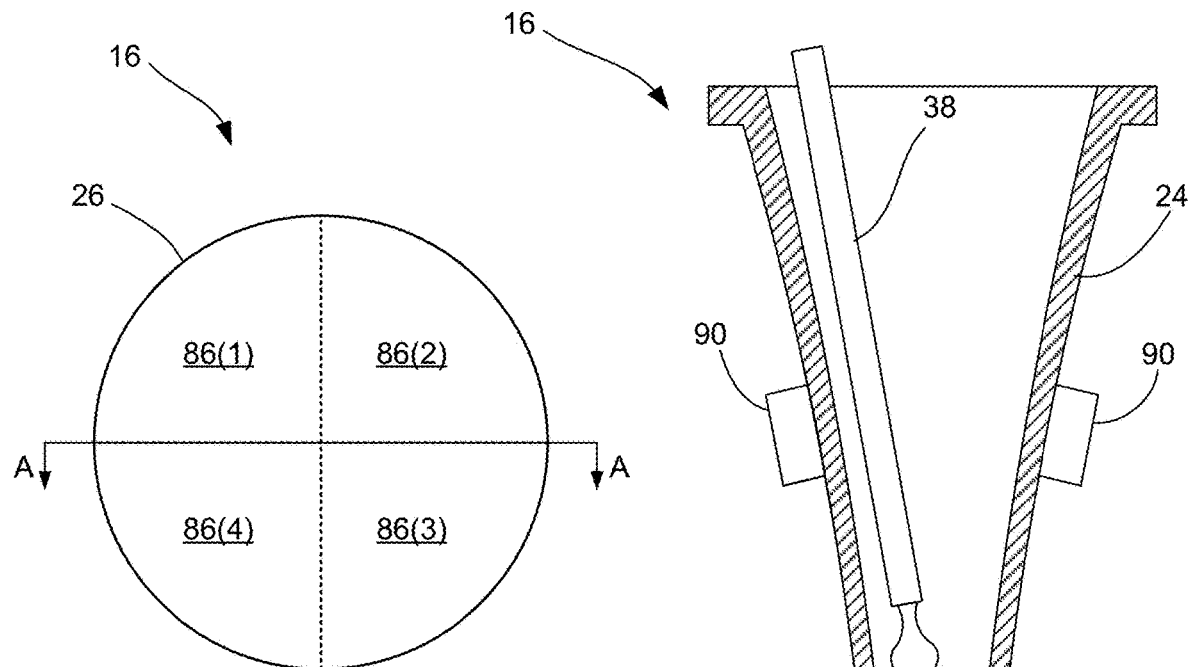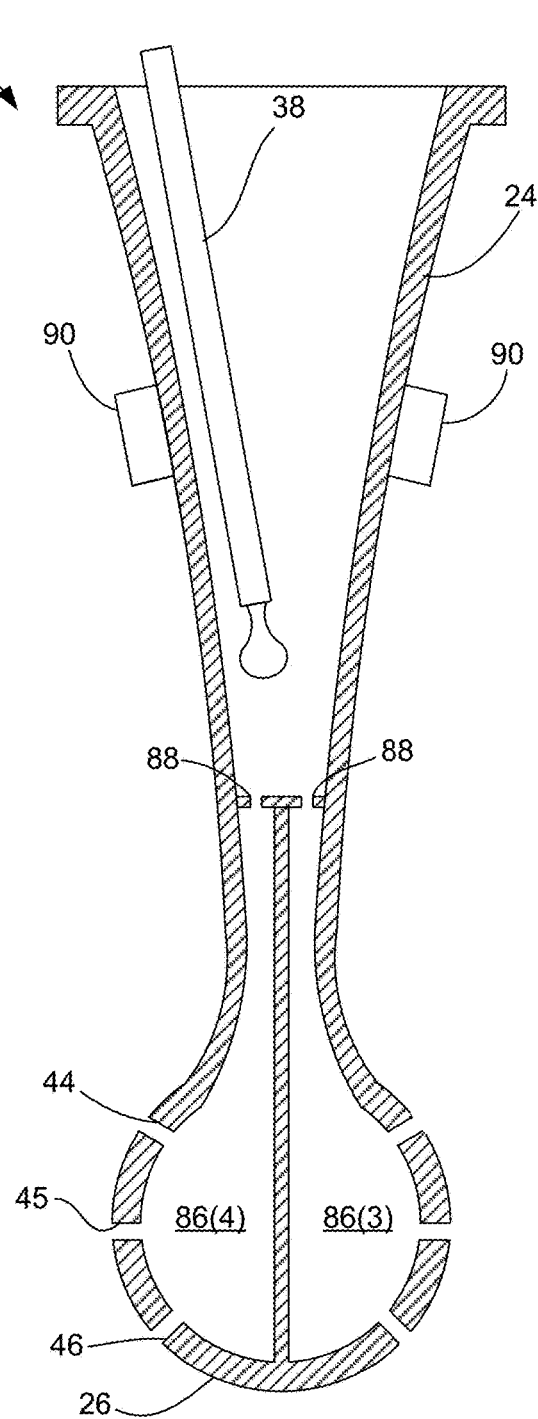
FIG. 13A
FIG. 13B

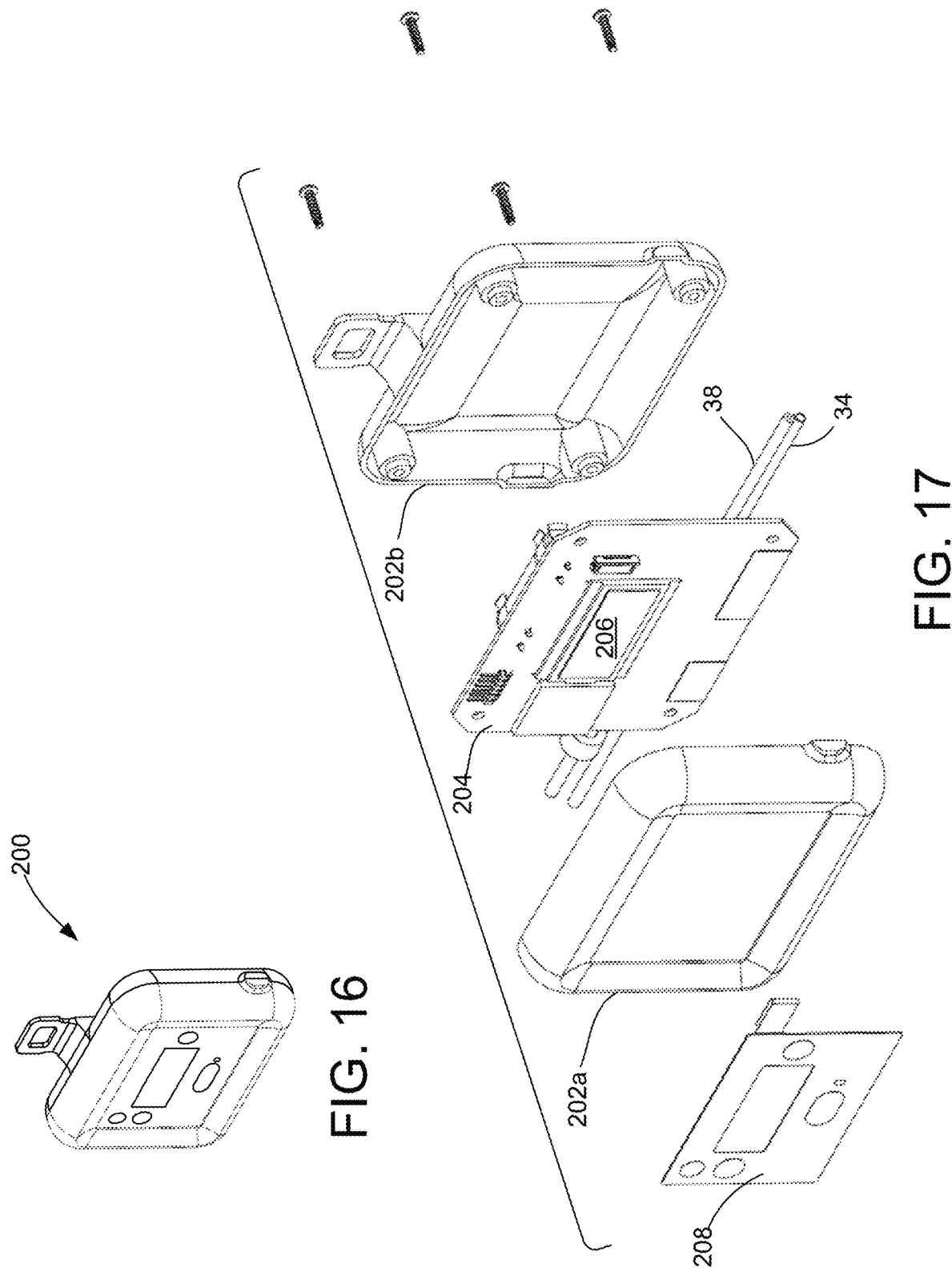

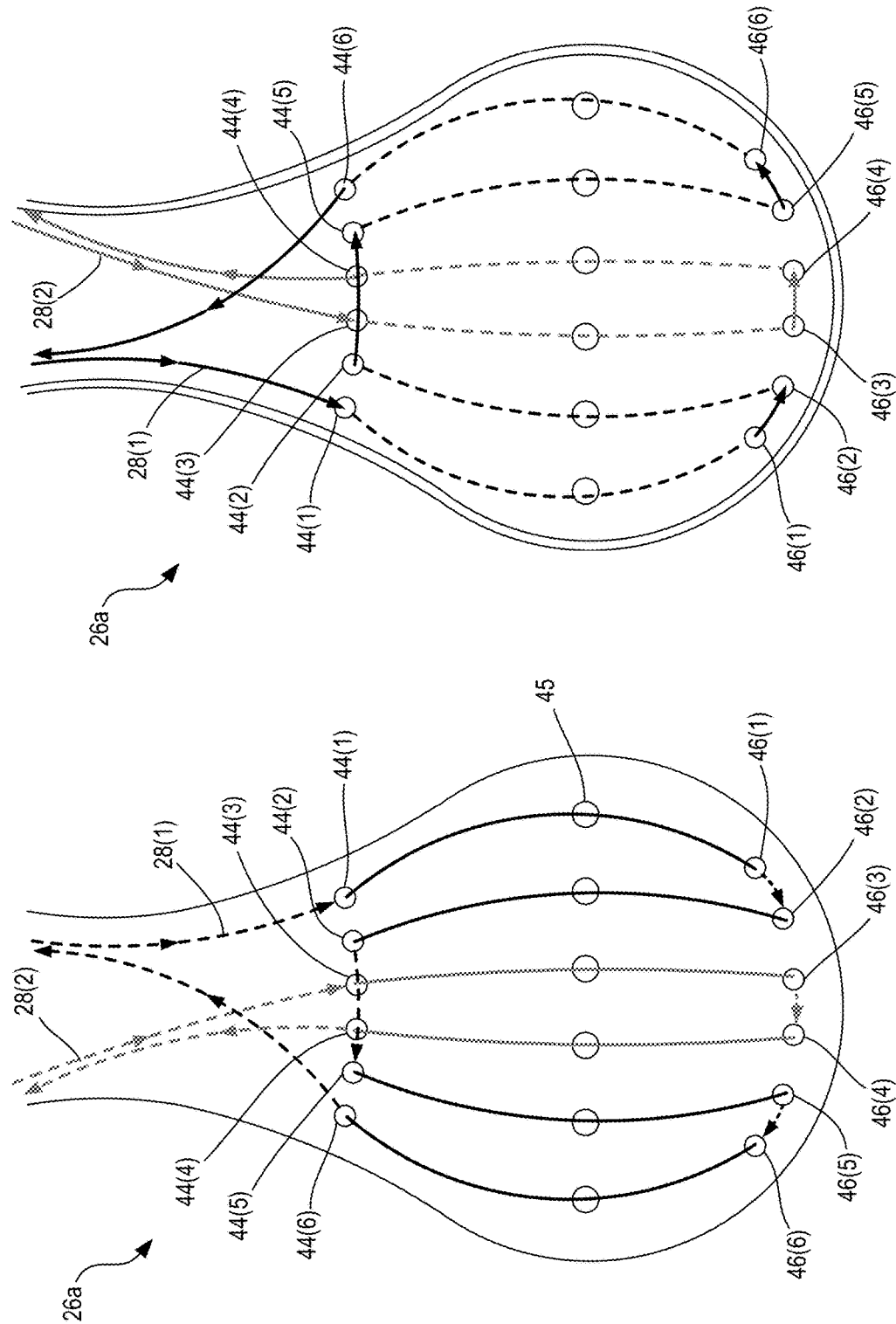

CAVITARY TISSUE ABLATION SYSTEM

CROSS-REFERENCE TO RELATED APPLICATIONS

This application claims the benefit of, and priority to, U.S. Provisional Application No. 62/290,108, filed Feb. 2, 2016, the content of which is incorporated by reference herein in its entirety.

FIELD

The present disclosure relates generally to medical devices, and, more particularly, to system for monitoring and controlling an ablation device to cause the ablation device to emit energy in a desired shape or pattern so as to deliver treatment for the ablation and destruction of a targeted portion of marginal tissue around the tissue cavity.

BACKGROUND

Cancer is a group of diseases involving abnormal cell growth with the potential to invade or spread to other parts of the body. Cancer generally manifests into abnormal growths of tissue in the form of a tumor that may be localized to a particular area of a patient's body (e.g., associated with a specific body part or organ) or may be spread throughout. Tumors, both benign and malignant, are commonly treated and removed via surgical intervention, as surgery often offers the greatest chance for complete removal and cure, especially if the cancer has not spread to other parts of the body. Electrosurgical methods, for example, can be used to destroy these abnormal tissue growths. However, in some instances, surgery alone is insufficient to adequately remove all cancerous tissue from a local environment.

For example, treatment of early stage breast cancer typically involves a combination of surgery and adjuvant irradiation. Unlike a mastectomy, a lumpectomy removes only the tumor and a small rim (area) of the normal tissue around it. Radiation therapy is given after lumpectomy in an attempt to eradicate cancer cells that may remain in the local environment around the removed tumor, so as to lower the chances of the cancer returning. However, radiation therapy as a post-operative treatment suffers various shortcomings. For example, radiation techniques can be costly and time consuming, and typically involve multiple treatments over weeks and sometimes months. Furthermore, radiation often results in unintended damage to the tissue outside the target zone. Thus, rather than affecting the likely residual tissue, typically near the original tumor location, radiation techniques often adversely affect healthy tissue, such as short and long-term complications affecting the skin, lungs, and heart.

Accordingly, such risks, when combined with the burden of weeks of daily radiation, may drive some patients to choose mastectomy instead of lumpectomy. Furthermore, some women (e.g., up to thirty percent (30%)) who undergo lumpectomy stop therapy before completing the full treatment due to the drawbacks of radiation treatment. This may be especially true in rural areas, or other areas in which patients may have limited access to radiation facilities.

SUMMARY

Tumors, both benign and malignant, are commonly treated and destroyed via surgical intervention, as surgery often offers the greatest chance for complete removal and cure, especially if the cancer has not metastasized. However, after the tumor is destroyed, a hollow cavity may remain, wherein tissue surrounding this cavity and surrounding the original tumor site can still leave abnormal or potentially cancerous cells that the surgeon fails, or is unable, to excise. This surrounding tissue is commonly referred to as "margin tissue" or "marginal tissue", and is the location within a patient where a reoccurrence of the tumor may most likely occur.

Some alternative treatments to using radiation therapy include the use of ablation devices to be inserted within cavitary excisional beds and deliver radiofrequency (RF) energy to marginal tissue surrounding the cavity following the procedure. For example, one type of proposed ablation applicator includes a long rigid needle-based electrode applicator for delivery of RF energy to marginal tissue upon manual manipulation by a surgeon or operator. Another type of ablation application includes an umbrella-type array of electrodes jointly connected to one another and deployable in an umbrella-like fashion to deliver RF energy.

While current ablation devices may provide some form tissue ablation, none have proven to meet all needs and circumstances encountered when performing marginal cavity tissue ablation. For example, in certain instances, it may be desirable to create a non-uniform ablation within a tissue cavity. In some instances, vital organs or critical internal/external structures (e.g., bone, muscle, skin, etc.) may be in close proximity to a tissue cavity and any unintended exposure to RF energy could have a negative impact.

Current RF ablation devices are unable to provide precise control over the emission of RF energy such that they lack the ability to effectively prevent emission from reaching vital organs or important internal/external structures during the ablation procedure. In particular, the long rigid needle-based electrode RF applicators generally require the surgeon or operator to manually adjust needle locations, and possibly readjust several electrodes multiple times, in order to control an ablation, which may lead to inaccuracy and difficulty in directing RF emission. The umbrella array RF applicators are limited by their physical geometry, in that the umbrella array may not be designed to fit within a cavity. Additionally, or alternatively, the uniform potential distribution of an umbrella array, as a result of the electrodes being jointly connected to one another, results in a tissue ablation geometry that is not adjustable without physically moving the umbrella array, thus resulting in similar problems as long rigid needle-based RF applicators.

The system of the present disclosure can be used during an ablation procedure to monitor ablation progress and to further control an ablation device in such a manner so as to cause the ablation device to emit energy in a desired shape or pattern so as to deliver treatment for the ablation and destruction the thin rim of marginal tissue around the cavity in a targeted manner.

In particular, the present disclosure is generally includes a controller configured to selectively control energy emission from an electrode array of an ablation device based on ablation feedback received during an ablation procedure with the ablation device. The controller is configured to receive feedback data from one or more sensors during an ablation procedure. The feedback data includes one or more measurements associated with at least one of operation of the electrode array of the ablation device and tissue adjacent to the electrode array. The system may include an ablation tracking interface module configured to receive the feedback data.

The measurements of the feedback data may include, but is not limited to, an elapsed time during an ablation period, electrical conductivity or complex impedance associated with one or more conductive wires of the electrode array of the ablation device, electrical current supplied to the one or more conductive wires, temperature of tissue adjacent to the electrode array, photonic properties of the tissue adjacent to the electrode array, and a combination thereof. Accordingly, in some embodiments, the system may further include at least one of a temperature sensor, voltage sensor, signal detector, and impedance sensor configured to obtain measurements during an ablation procedure.

The controller is further configured to generate an ablation pattern for controlling energy emission from the electrode array of the ablation device in response to the received feedback data. The ablation pattern may include, but is not limited to, a selected one or more conductive wires from a plurality of conductive wires of the electrode array, to receive electrical current for energy emission, a level of electrical current to be supplied to a selected one or more conductive wires, a length of elapsed time during which electrical current is to be supplied to a selected one or more conductive wires, one or more intervals over which electrical current is to be supplied to a selected one or more conductive wires, and a combination thereof.

The electrode array of the ablation device may include a plurality of independent conductive wires configured to independently receive electrical current. Accordingly, in some embodiments, the ablation pattern may include a selected one, or a selected set of two or more, of the plurality of conductive wires resulting in emission of energy therefrom corresponding to a portion of the electrode array, thereby resulting in targeted ablation of adjacent tissue.

The generation of the ablation pattern may include processing the feedback data in real-, or near-real-, time and generating ablation status mapping based on the processed feedback data. The ablation status mapping provides an estimation of the state of the tissue to be ablated, currently undergoing ablation, or having undergone ablation. The generation of the ablation status mapping may include processing of the feedback data in accordance with at least the formula: (t, s, init_local_Z[ ], init_global_Z[ ], current_local_Z[ ], current_global_Z[ ], x, y, z)→AblationStatus, wherein 't' indicates an elapsed time in seconds, 's' indicates a size of an ablating end of the ablation device, 'Z' indicates impedance, 'H' indicates arrays with length of a number of conductive wires, and 'x,y,z' are coordinates of a sub volume of tissue.

The generation of the ablation pattern may further include a combination of ablation status mapping data with an electrode activation algorithm for assignment of one or more ablation control parameters for selective conductive wire activation for subsequent targeted ablation of adjacent tissue. Accordingly, the system may include an ablation mapping module and an ablation geometry shaping module, the ablation mapping module configured to receive and process the feedback data and transmit mapping data to the ablation geometry shaping module configured to process the mapping data to generate the ablation pattern. The ablation geometry shaping module may be configured to transmit the ablation pattern to an electrode connection multiplexer controller, which is configured to supply electrical current to a selected one, or set of two or more, conductive wires in response to the ablation pattern.

The devices, systems, and methods of the present disclosure can help to ensure that all microscopic disease in the local environment has been treated. This is especially true in the treatment of tumors that have a tendency to recur. Furthermore, by providing custom ablation shaping, in which the system can control a single ablation device to provide numerous RF energy emission shapes or profiles, the system of the present invention allows for non-uniform ablation to occur. This is particularly useful in controlling ablation shape so as to avoid vital organs and any critical internal/external structures (e.g., bone, muscle, skin) in close proximity to the tumor site, while ensuring that residual marginal tissue within the local environment has been treated.

It should be noted the devices of the present disclosure are not limited to such post-surgical treatments and, as used herein, the phrase "body cavity" may include non-surgically created cavities, such as natural body cavities and passages, such as the ureter (e.g. for prostate treatment), the uterus (e.g. for uterine ablation or fibroid treatment), fallopian tubes (e.g. for sterilization), and the like. Additionally, or alternatively, tissue ablation devices of the present disclosure may be used for the ablation of marginal tissue in various parts of the body and organs (e.g., lungs, liver, pancreas, etc.) and is not limited to treatment of breast cancer.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 1 is a schematic illustration of an ablation system consistent with the present disclosure;

FIGS. 8A, 8B, 8C, 8D, and 8E are perspective views of a distal tip of the ablation device of FIG. 1 illustrating various electrode array configurations;

FIG. 13A is a front view of one embodiment of a distal tip of the ablation device of FIG. 12 illustrating one or more chambers formed within the distal tip;

FIG. 13B is a sectional view of one embodiment of the ablation device of FIG. 12 taken along lines A-A, illustrating at least two of the chambers within the distal tip;

FIGS. 16 and 17 are perspective and exploded perspective views, respectively, of one embodiment of a device controller consistent with the present disclosure;

FIGS. 21A and 21B are enlarged views of the spheroid body of the first halve of the device showing the exterior and interior surfaces, respectively, and further illustrating the particular arrangement of first and second conductive wires extending through proximal and distal ports of the spheroid body;

Figure 2:
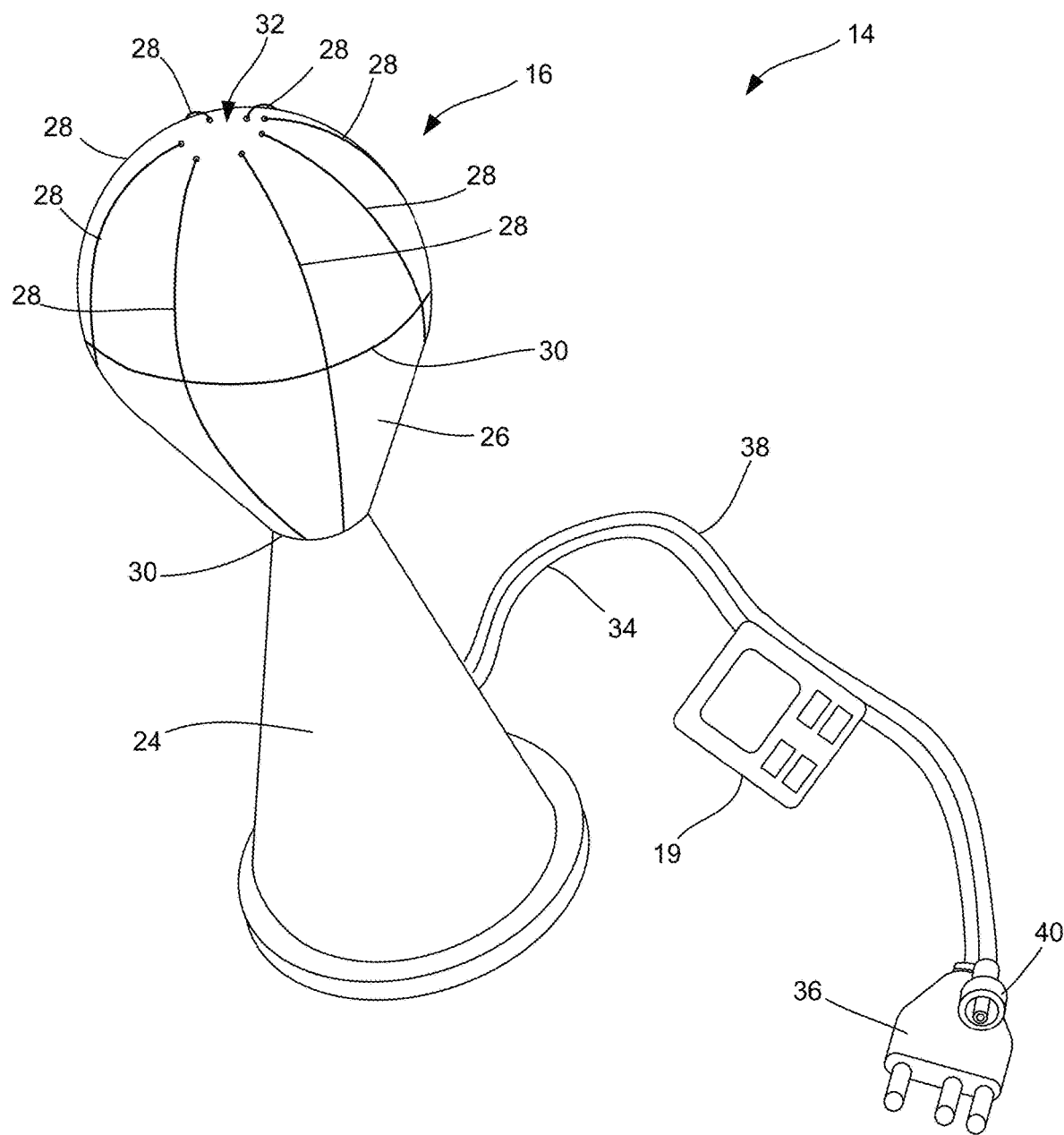
FIG. 2 is a perspective view of an ablation device tip of the ablation system of FIG. 1.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a system for monitoring and controlling an ablation device to cause the ablation device to emit energy in a desired shape or pattern so as to deliver treatment for the ablation and destruction of a targeted portion of marginal tissue around the tissue cavity.

In particular, the present disclosure is generally includes a controller configured to selectively control energy emission from an electrode array of an ablation device based on ablation feedback received during an ablation procedure with the ablation device. The controller is configured to receive feedback data from one or more sensors during an ablation procedure. The feedback data includes one or more measurements associated with at least one of operation of the electrode array of the ablation device and tissue adjacent to the electrode array. The controller is further configured to generate an ablation pattern for controlling energy emission from the electrode array of the ablation device in response to the received feedback data.

The devices, systems, and methods of the present disclosure can help to ensure that all microscopic disease in the local environment has been treated. This is especially true in the treatment of tumors that have a tendency to recur. Furthermore, by providing custom ablation shaping, in which the system can control a single ablation device to provide numerous RF energy emission shapes or profiles, the system of the present invention allows for non-uniform ablation to occur. This is particularly useful in controlling ablation shape so as to avoid vital organs and any critical internal/external structures (e.g., bone, muscle, skin) in close proximity to the tumor site, while ensuring that residual marginal tissue within the local environment has been treated.

It should be noted the devices of the present disclosure are not limited to such post-surgical treatments and, as used herein, the phrase "body cavity" may include non-surgically created cavities, such as natural body cavities and passages, such as the ureter (e.g. for prostate treatment), the uterus (e.g. for uterine ablation or fibroid treatment), fallopian tubes (e.g. for sterilization), and the like.

FIG. 1 is a schematic illustration of an ablation system 10 for providing targeted ablation of marginal tissue during a tumor removal procedure in a patient 12. The ablation system 10 generally includes an ablation device 14, which includes a probe having a distal tip or portion 16 and an elongated catheter shaft 17 to which the distal tip 16 is connected. The catheter shaft 17 may generally include a nonconductive elongated member including a fluid delivery lumen. The ablation device 14 may further be coupled to a device controller 18 and an ablation generator 20 over an electrical connection (electrical line 34 shown in FIG. 2), and an irrigation pump or drip 22 over a fluid connection (fluid line 38 shown in FIG. 2).

As will be described in greater detail herein, the device controller 18 may further include a custom ablation shaping (CAS) system 100 configured to provide a user with custom ablation shaping, which includes the creation of custom, user-defined ablation geometries or profiles from the ablation device 14. In some cases, the device controller 18 may be housed within the ablation device 14. The ablation generator 20 may also connected to a return electrode 15 that is attached to the skin of the patient 12.

As will be described in greater detail herein, during an ablation treatment, the ablation generator 20 may generally provide RF energy (e.g., electrical energy in the radiofrequency (RF) range (e.g., 350-800 kHz)) to an electrode array of the ablation device 14, as contollered by the device controller 18. At the same time, saline may also be released from the distal tip 16. The RF energy travels through the blood and tissue of the patient 12 to the return electrode 112 and, in the process, ablates the region(s) of tissues adjacent to portions of the electrode array that have been activated.

FIG. 2 is a perspective view of the distal portion or tip 16 of the ablation device 14. The distal tip 16 may include a neck portion 24 and a generally spheroid body 26 extending distally from the neck 24. It should be noted that, in some embodiments, the spheroid body 26 may be configured to transition between a collapsed state and an expanded state. For example, the spheroid body 26 may be collapsible to a delivery configuration having a reduced size (e.g., equatorial diameter) relative to the deployed configuration size (e.g., equatorial diameter) of the spheroid body 26. In some examples, the spheroid body 26 is a generally prolate-spheroid during delivery and transitions to a spheroid shape during deployment. In other embodiments, the spheroid body 26 may be rigid, and thus may maintain a default shape.

In some examples, the spheroid body 26 includes a non-conductive material (e.g., a polyamide) as a layer on at least a portion of an internal surface, an external surface, or both an external and internal surface. In other examples, the spheroid body 26 is formed from a non-conductive material. Additionally or alternatively, the spheroid body 26 material can include an elastomeric material or a shape memory material.

In some examples, the spheroid body 26 has a diameter (e.g., an equatorial diameter) of about 80 mm or less. In certain implementations, the spheroid body 26 of the distal tip, in a deployed configuration, has an equatorial diameter of 2.0 mm to 60 mm (e.g., 5 mm, 10 mm, 12 mm, 16 mm, 25 mm, 30 mm, 35 mm, 40 mm, 50 mm, and 60 mm). Based on the surgical procedure, the collapsibility of the spheroid body 28 can enable the distal tip to be delivered using standard sheaths (e.g., an 8F introducer sheath).

The distal tip 16 of the ablation device 14 further includes an electrode array positioned thereon. The electrode array includes at least one conductive member 28. As illustrated in the figures, the electrode array includes at least eight conductive members 28. Accordingly, the electrode array may include a plurality of conductive members 28. The plurality of conductive members 28 extend within the distal tip 16, through a channel 32 and along an external surface of the spheroid body 26. The conductive members 28 extend along the longitudinal length of the distal tip 16 and are radially spaced apart (e.g., equidistantly spaced apart) from each other. These conductive members transmit RF energy from the ablation generator and can be formed of any suitable conductive material (e.g., a metal such as stainless steel, nitinol, or aluminum). In some examples, the conductive members 28 are metal wires. Accordingly, for ease of description, the conductive member(s) will be referred to hereinafter as "conductive wire(s) 28".

As illustrated, one or more of the conductive wires 28 can be electrically isolated from one or more of the remaining conductive wires 28. This electrical isolation enables various operation modes for the ablation device 14. For example, ablation energy may be supplied to one or more conductive wires 28 in a bipolar mode, a unipolar mode, or a combination bipolar and unipolar mode. In the unipolar mode, ablation energy is delivered between one or more conductive wires 28 on the ablation device 14 and the return electrode 12, as described with reference to FIG. 1. In bipolar mode, energy is delivered between at least two of the conductive wires 28, while at least one conductive wire 28 remains neutral. In other words, at least, one conductive wire functions as a grounded conductive wire (e.g., electrode) by not delivering energy over at least one conductive wire 28.

The electrode array may further include one or more stabilizing members 30 configured to provide support for the plurality of conductive wires 28. The one or more stabilizing member 30 generally extend along a surface (e.g., external or internal) of the distal tip 16 so as to circumscribe the spheroid body 26. The stabilizing members 30 can, in some examples, electrically connect to one or more conductive wires 28. In other examples, the stabilizing members 30 are non-conductive. The stabilizing members 30 can be formed of a suitably stiff material (e.g., metal such as stainless steel, nitinol, or aluminum). In some implementations, the stabilizing members 30 can be integral with a portion of the spheroid body 26 (e.g., as a rib). While, the distal tip 16 is generally shown with one or more stabilizing members, in some implementations, the distal tip 16 is free of stabilizing members.

As shown, the distal tip 16 may be coupled to the ablation generator 20 and/or irrigation pump 22 via an electrical line 34 and a fluid line 38, respectively. Each of the electrical line 34 and fluid line 38 may include an adaptor end 36, 40 configured to couple the associated lines with a respective interface on the ablation generator 20 and irrigation pump 22. In some examples, the ablation device 14 may further include a user switch or interface 19 serving as the device controller 18 and in electrical communication with the ablation generator 20 and the ablation device 14. The switch 19 can provide a user with various options with respect to controlling the ablation output of the device 14, as will be described in greater detail herein. For example, the switch 19, which may serve as the device controller 18, may include a CAS system 100 configured to provide custom ablation shaping controls for a user to create custom, user-defined ablation geometries or profiles, as well as control particular ablation parameters, such as control of timing of the emission (e.g., length of time, intervals, etc.) as well as the depth of RF energy penetration. In some embodiments, the switch 19 may be configured to control energy delivery from the ablation generator 20 so that one or more individual conductive wires, or a designated combination of conductive wires, are energized for a pre-selected, or desired, duration.

Figure 3A:
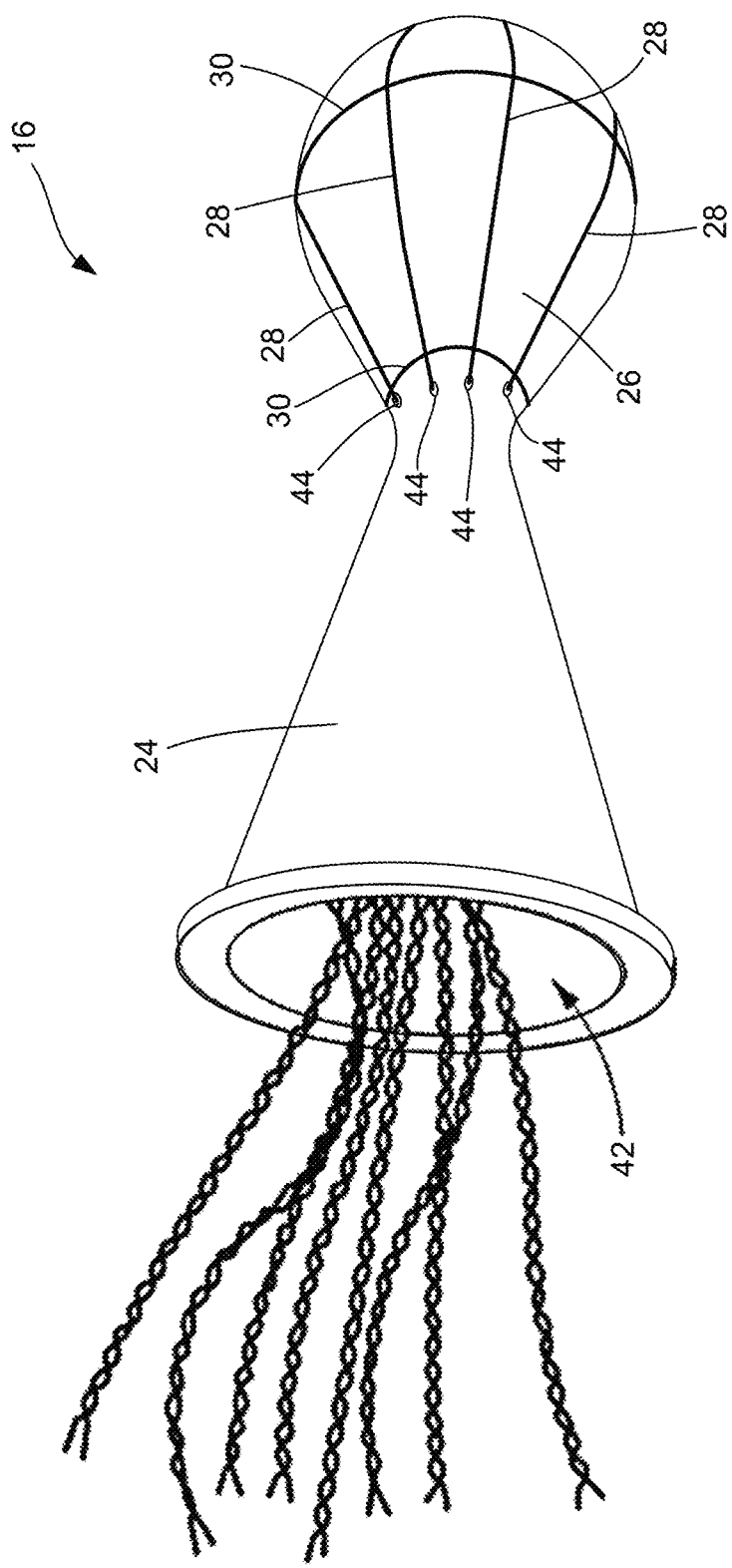
FIGS. 3A, 3B, and 3C are perspective views of the ablation device tip of FIG. 2 in greater detail.
Figure 3B:
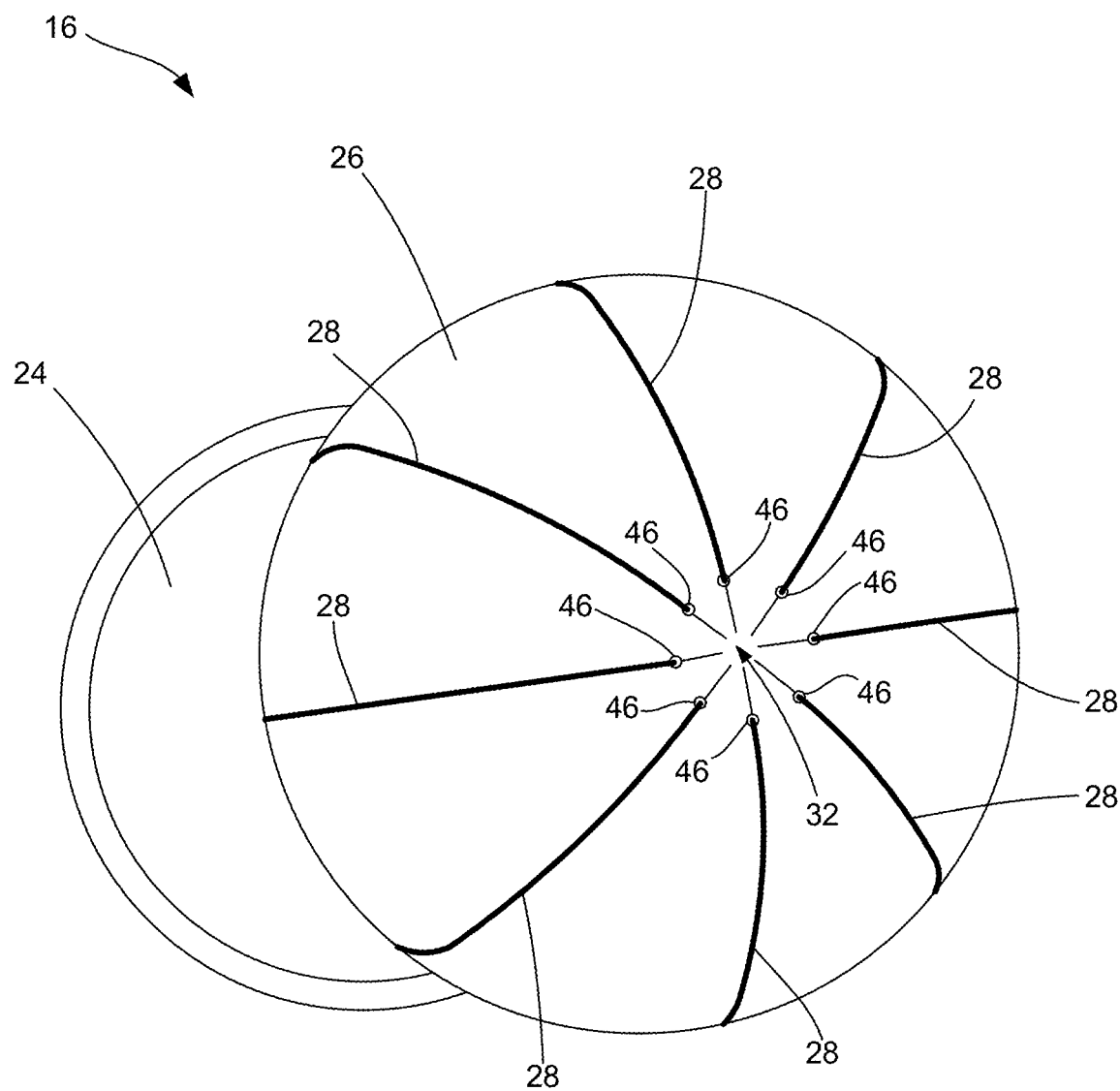
Figure 3C:
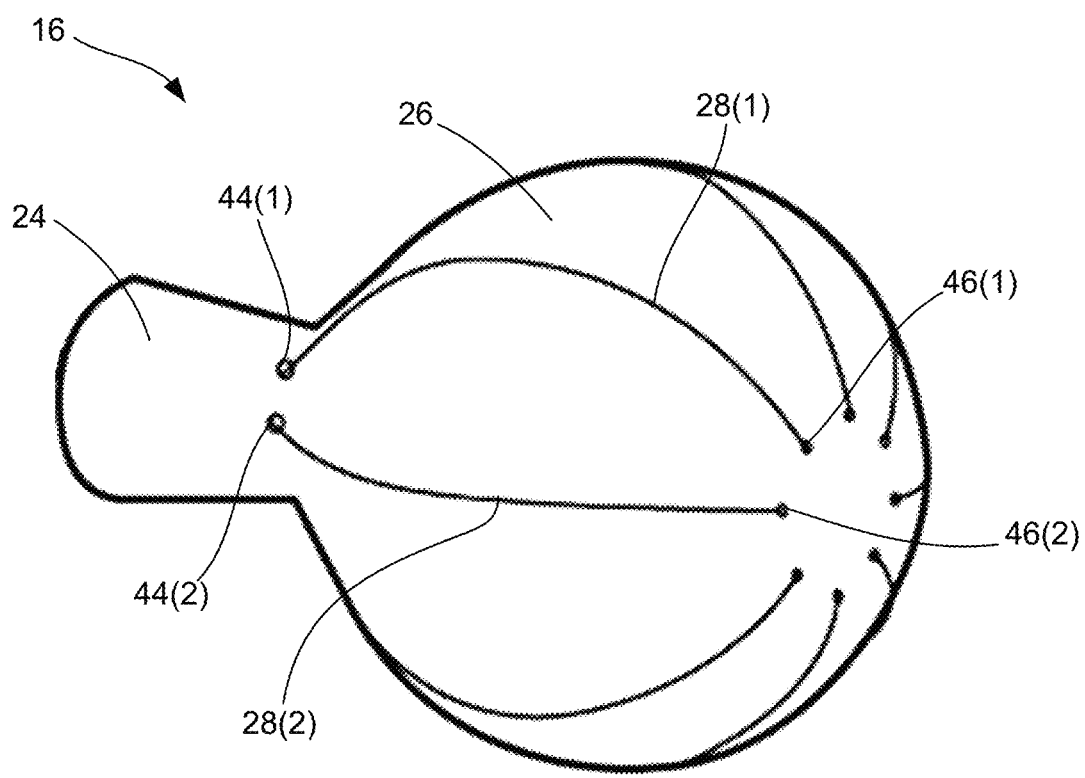

FIGS. 3A, 3B, and 3C are perspective views of the distal tip 16 of FIG. 2 in greater detail. As shown in FIGS. 2 and 3A-3C, the conductive wires 28 extend through a lumen 42 within the distal tip 16. For example, each of the conductive wires 28 enters the lumen 42 of the neck 27 and extends through the distal tip portion 16 before exiting the distal tip through either a center channel 32 at a distal most portion of the distal tip or one of a plurality of proximal ports 44. In some examples, a plurality of distal ports 46 extending through a wall of the distal tip 16 is positioned around the channel 32. A plurality of proximal ports 44 can also extend through a wall of the distal tip 16. These proximal ports 44 can be positioned around the distal tip 16 in close proximity (e.g., within at least 5 mm, within at least 3 mm, within at least 1 mm, within 0.5 mm, within 0.4 mm, or within 0.2 mm) to the junction between the spheroidal body 26 and the neck 24 of the distal tip 16. In some cases, the number of proximal ports 44 and distal ports 46 is equal to the number of conductive wires 28.

In some examples, each conductive wire 28 can extend through a different distal port 46, which allows the conductive wires 28 to remain electrically isolated from one another. In other examples, one or more conductive wires can extend through the same distal port 46.

Upon passing through a distal port 46, each conductive wire 28 can extend along an external surface of the distal tip 16. In some examples, the length of the conductive wire 28 extending along the external surface is at least 20% (e.g., at least, 50%, 60%, 75%, 85%, 90%, or 99%) of the length of the spheroid body 26. The conductive wire 28 can then re-enter the lumen 42 of the distal tip 16 through a corresponding proximal port 44. For example, as shown in FIG. 3C, conductive wire 28(1) passes through distal port 46(1), extends along a length of the external surface of the distal tip 16, and passes through an associated proximal port 44(1) into the lumen 42 of the distal tip 16, while conductive wire 28(2) is electrically isolated from conductive wire 28(1) in that it passes through associated proximal and distal ports 44(2), 46(2), respectively.

In some examples, each conductive wire 28 can extend through a different associated proximal port 44, which allows the conductive wires 28 to remain electrically isolated from one another. In other examples, one or more conductive wires can extend through the same proximal port. Yet still, as will be described in greater detail herein, particularly with reference to the device 14a illustrated in FIGS. 21A-21B and 22A-22B, an individual conductive wire can extend through multiple proximal and distal ports.

Figure 4:
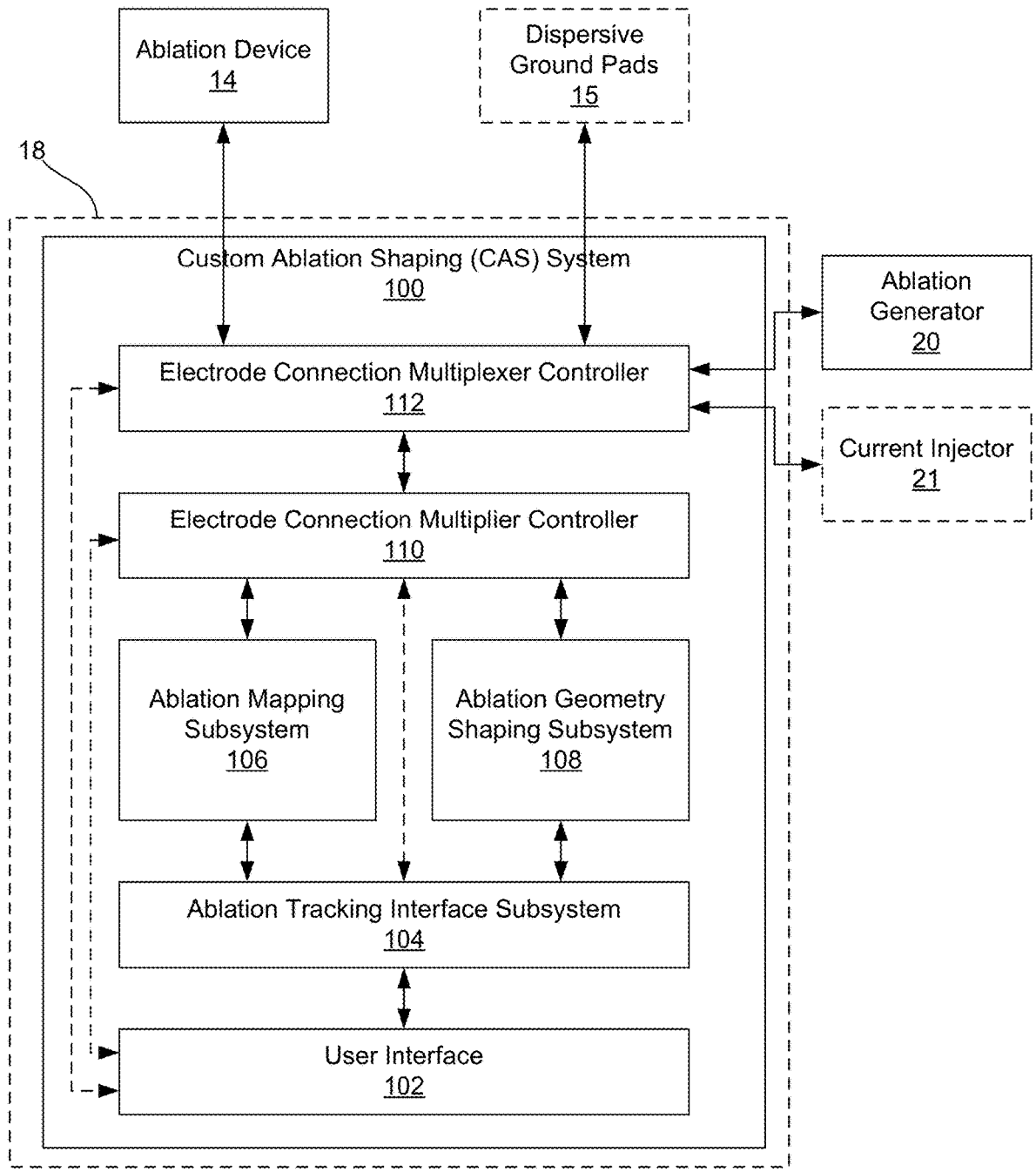
FIG. 4 is a block diagram illustrating the custom ablation system of the device controller in greater detail.

FIG. 4 is a block diagram illustrating the custom ablation shaping (CAS) system 100 of the device controller 18. As previously described herein, the electrode array is composed of a plurality of conductive wires 28 electrically isolated and independent from one another. This design allows for each conductive wire 28 to receive energy in the form of electrical current from the ablation generator 20 and emit RF energy in response. The device controller 18 is configured to selectively control the supply of electrical current to each of the conductive wires via the CAS system 100.

The CAS system 100 includes one or more of the following: a user interface 102; an ablation tracking interface subsystem 104; an ablation mapping subsystem 106; an ablation geometry shaping subsystem 108; an electrode connection multiplier controller 110; and an electrode connection multiplexer controller 112. It should be noted that the dashed connections (between the user interface 102 and electrode connection multiplier controller 110 and the electrode connection multiplexer controller 112) indicate fail-safes and out-of-band control lines not used, or intended for use, during normal operation. However, in the event that one or more of the components fail to operate as intended, the user may override such components so as to directly control activation of one or more conductive wires 28.

As previously described, the specific design of the electrode array (e.g., plurality of conductive wireselectrically isolated and independent from one another) allows for each conductive wire to receive energy in the form of electrical current from the ablation generator 20 and emit RF energy in response. In particular, the device controller 18 allows for individual conductive wires, or a designated combination of conductive wires, to be controlled so as to result in the activation (e.g., emission of RF energy) of corresponding portions of the electrode array.

In some embodiments, the device controller 18, specifically by way of the CAS system 100, provides a user with the ability to manually control the supply of electrical current to each of the conductive wires. More specifically, the user interface 102 may provide a user with the ability to create custom ablation shapes or patterns, or further manipulate ablation parameters (e.g., timing and intensity) via an interactive interface, which may be in the form of a graphical user interface (GUI) provided on a display of the device controller 18 or switch 19. Accordingly, as will be described in greater detail herein (shown in FIGS. 5, 6A-6B, and 7A-7B), the CAS system 100 may allow a user to manually control emission from the electrode array and customize the ablation shape or geometry as they see fit.

In other embodiments, the CAS system 100 may be configured to automatically provide custom ablation shaping in addition, or alternatively, to manual input from a user. For example, the device controller 18 may be configured to provide ablation status mapping based on real-time data collection (e.g., temperature and conductivity measurements (impedance measurements) from one or more of the conductive wires) so as to provide an estimation of the state of the tissue during an RF ablation procedure. The CAS system 100 is configured to generate ablation status mapping of a target tissue based, at least in part, on characterizing temporal changes in conductivity of a target tissue during ablation and correlating such changes with temperature and cell viability. The ablation status mapping may then be combined with an electrode activation algorithm for the assignment of parameters for selective electrode activation for ablation shaping. Accordingly, the automatic custom ablation shaping feature of the present invention allows for spatial resolution of the ablation mapping and shaping systems to occur in vitro and further determine the depths from the electrode which the mapping/sensing system can make reliable estimations. Thus, the system can compensate ablation progression during control parameter calculations so as to provide more accurate ablation of a target tissue while avoiding any vital organs or critical internal/external structures in close proximity to the target tissue.

In order to achieve the capability of ablation status mapping, the CAS system 100 is configured to collect data for a machine learning model and then use the model to map ablation status in real time. The data collected includes, but is not limited to, temperature measurements, conductivity or impedance measurements, and photonic properties of the target tissue. By measuring time and the change in impedance (real or complex), temperature, and/or photonic properties of the target tissue, the CAS system 100 is configured to determine the ablation shape or geometry (energy emission from electrode array) in real-, or near-real-, time.

Since each conductive wire in the electrode array is electrically independent, each conductive wire can be connected in a fashion that allows for impedance measurements using bipolar impedance measurement circuits. For example, the conductive wires can be configured in such a fashion that tetrapolar or guarded tetrapolar electrode configurations can be used. For instance, one pair of conductive wires could function as the current driver and the current return, while another pair of conductive wires could function as a voltage measurement pair. The dispersive ground pads 15 can also function as current return and voltage references. Their placement dictate the current paths and thus having multiple references can also benefit by providing additional paths for determining the ablation status of the tissue.

The electrode connection multiplexer controller 112 is configured to collect the data in the form of local impedances (impedances between conductive wires on the distal tip) and global impedances (impedances between conductive wires and global dispersive return 15) and further transmit such data to the ablation mapping subsystem 106. A Kelvin electrode configuration driven with 500 µA at 200 kHz (for filtering from the 470 kHz RF signal) may be used in order to measure these impedances.

The ablation mapping subsystem 106 is configured to analyze the impedance data with time elapsed in order to form a judgment of the ablation status of certain parts of the entire ablation volume. In particular, the ablation mapping subsystem 106 may include custom, proprietary, known and/or after-developed analysis code (or instruction sets), hardware, and/or firmware that are generally well-defined and operable to receive one or more sets of data and estimate an ablation status of local target tissue sub volumes based on analysis of such data. Thus, the ablation mapping subsystem 106 may utilize a specific input model in order to output an ablation status integer for any sub volume of the ablation volume. The input model is as follows:

$$(t, s, \text{init\_local\_Z[ ]}, \text{init\_global\_Z[ ]}, \text{current\_local\_Z[ ]}, \text{current\_global\_Z[ ]}, x, y, z) \rightarrow \text{AblationStatus}$$

where 't' indicates time in seconds, 's' indicates the size of the applicator (diameter, area, volume, etc. of the distal tip), 'Z' indicates impedance, 'H' indicates arrays with length of the number of conductive wires, and 'x,y,z' are the coordinates of the sub volume.

As in the input model provided above, each sub volume the ablation map may include five possible statuses: "0" indicating no ablation occurring, "1" indicating that heating is occurring, "2" indicating that instantaneous ablation or coagulation has begun (the tissue has reached a temperature of 60° C.), "3" indicating that ablation has occurred, and "4" indicating that desiccation (vaporization) is occurring. In order to develop the classification model, benchtop ablations are performed where the following training data is collected: time, init_local_Z[ ], init_global_Z[ ], current_local_Z[ ], current_global_Z[ ], and for a set of radii (0.25, 0.5, 0.75, 1.0, 1.25, 1.5 cm) surrounding the applicator, the exact temperature, which translates to the ablation status (0 for initial temperature, 1 for ≥40° C., 2 for ≥50° C., 3 for ≥60° C., 4 for ≥100° C.). This method of ablation mapping is also designed to be mostly heterogeneity-invariant, since local impedances are inputs into the model, which treat the heterogeneous tissues as different tissue types present.

In order to obtain reference tissue ablation parameters, the training data may then be input into multiple supervised machine learning algorithms, where the most accurate classifier will be used for the real-time system. Training data may be collected within ex vivo bovine and porcine liver blocks of 10 cm by 10 cm by 10 cm. The tissue can be placed in a saline bath such that the global ground is simulated as far-field to prevent optimistic global impedance measurements. Verifications on the classifier will be performed after the model is learned to ensure success criteria, including controls with and without RF energy applied.

The target endpoint is 90% accuracy (with zero false ablated statuses) of ablation status mapping with 1.0 mm of spatial sub volume resolution for the local field (≤1.0 cm depth from applicator surface). Additional success criteria may include the accuracy of ablation status mapping up to 3.0 mm sub volume resolution into the sub global field (1.0-2.0 cm depth from applicator surface).

If the classifier fails to classify based only on initial and changes in impedance, then an additional parameter, the estimated local tissue conductivity, will be added to the model. The estimated conductivity is covered within the model by the initial and early-time impedances, but a more explicit variable may be required. If the target endpoint spatial resolutions failed to be realized, then the electrodes will be increased in number to increase density for higher spatial resolution.

The ablation geometry shaping subsystem 108 is configured to receive output data from the ablation mapping subsystem 106, specifically ablation status mapping data via the ablation tracking interface subsystem 104, and determine a specific ablation shape or geometry to output (e.g., identify specific conductive wires or combination of conductive wires to apply power to and the specific parameters) in order to achieve the desired custom ablation shape based on the ablation status mapping. In particular, the ablation geometry shaping subsystem 108 may rely on an electrode activation algorithm necessary to operate the network of solid-state relays (also known as a crossbar) that connect the conductive wires to the radiofrequency power generator 20. The ablation geometry shaping subsystem 108 may generate ablation shape data based on processing of the ablation status mapping data via the electrode activation algorithm.

The ablation geometry shaping subsystem 108 may then transmit ablation shape data to the electrode connection multiplexer controller 112 for activation of specific conductive wires, or combinations of conductive wires, so as to achieve the desired ablation shape. For example, the electrode connection multiplier controller 110 may be configured to physically operate solid-state relays on the electrode connection multiplexer (the electrode-switching/power-switching circuit), connecting the electrodes needed to RF power. By time-division multiplexing, different conductive wires in a manner similar to pulse width modulation (PWM), where the conductive wires are connected to power for a specified duration and then disconnected in a repeated pattern. Time-multiplexing may be especially important for deeper ablations that are geometrically between multiple conductive wires, in which the theoretical circuit relies on heat transfer to nearby (i.e., not currently electrically-conducting) tissues and only the concentration of heat in the desired zone due to the combined efforts of the conductive wires activating in the multiplexed fashion.

The ablation mapping subsystem 106 and ablation geometry shaping system 108 may be configured to continuously operate during a procedure so as to provide up-to-date information which may further improve the accuracy and safety of the ablation procedure. For example, ablation status mapping data may be continuously generated and fed into the ablation geometry shaping system 108 so as to continuously generate ablation shaping data, which may be used to either validate the current ablation energy applied, or to update or correct the ablation shape (i.e., indicate where to continue ablation or when to stop ablation). It should further be noted that ablation mapping status can be displayed to a user using a 3D visualization, which can be controlled by the user interface 102 (e.g., touchscreen or the like) similar to a 3D map application. Each layer of tissue may be displayed as being somewhat transparent so as to allow for the operator to see which regions are ablated and which are not.

Figure 5:
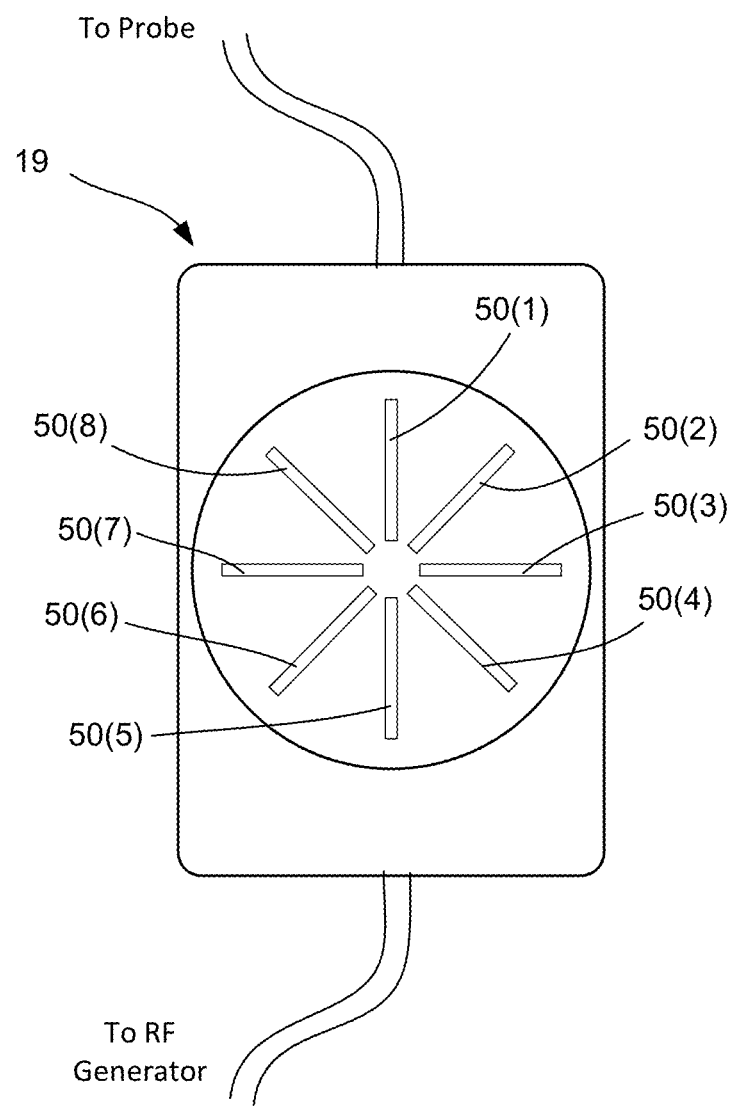
FIG. 5 is a top view of one embodiment of device controller configured for individually controlling operational modes of each of the plurality of conductive wires of the electrode array of the ablation device tip.

As previously described, the device controller 18 may be configured to be operated manually, such that a user (e.g., surgeon or operator) may input desired ablation shape or pattern and associated parameters. FIG. 5 is a top view of one embodiment of device controller 19 configured for individually controlling operational modes of each of the plurality of conductive wires of the electrode array of the ablation device tip. The controller 19 may provide selectable inputs 50(1)-50(8) in which a user may turn individual conductive wires, or one or more combinations of conductive wires, on and off, thereby allowing a user to control an ablation shape or geometry. As shown, the selectable inputs 50(1)-50(8) may correspond to the eight individual conductive wires 28(1)-28(8) of the distal tip 16 (see FIGS. 6A-6B and 7A-7B). Accordingly, activation of any one of the selectable inputs 50 may result in the activation of corresponding conductive wires 28.

Figure 6A:
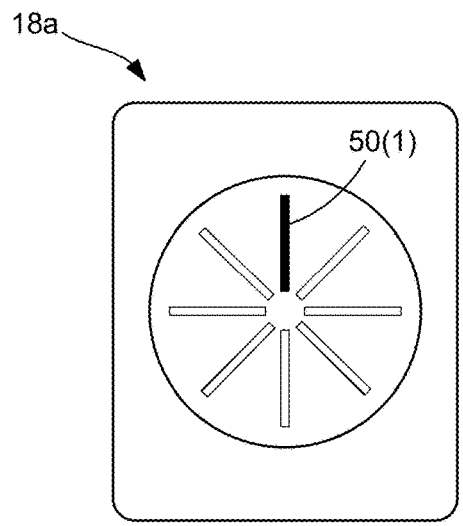
FIG. 6A is a top view of the device controller in a first mode and FIG. 6B is a front view of the ablation device tip illustrating the electrode array operating in the first mode.
Figure 6B:
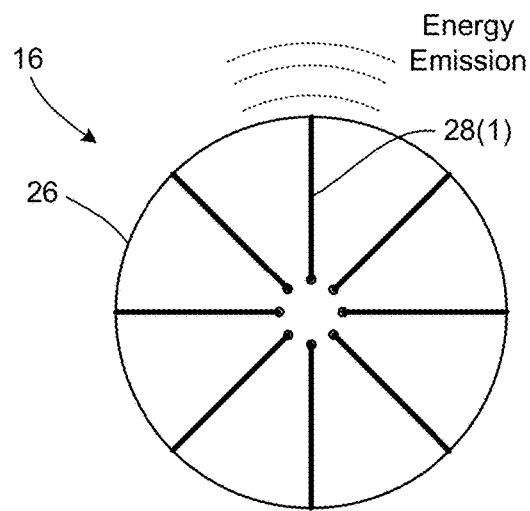

FIG. 6A is a top view of the device controller 19 with inputs 50 in a first mode and FIG. 6B is a front view of the ablation device tip illustrating the electrode array operating in the first mode. As shown, input 50(1) is selected and, in turn, the corresponding conductive wire 28(1) is activated (current supplied thereto and RF energy emitted). Accordingly, the electrode array may be configured to operate in a monopolar mode in which individual conductive wires may be activated.

Figure 7A:
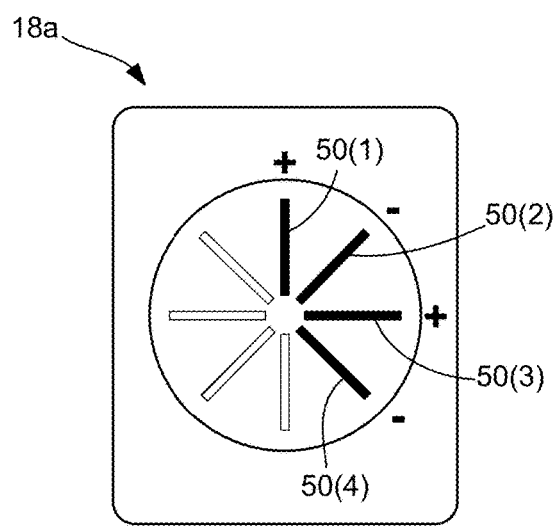
FIG. 7A is a top view of the device controller in a second mode and FIG. 7B is a front view of the ablation device tip illustrating the electrode array operating in the second mode.
Figure 7B:
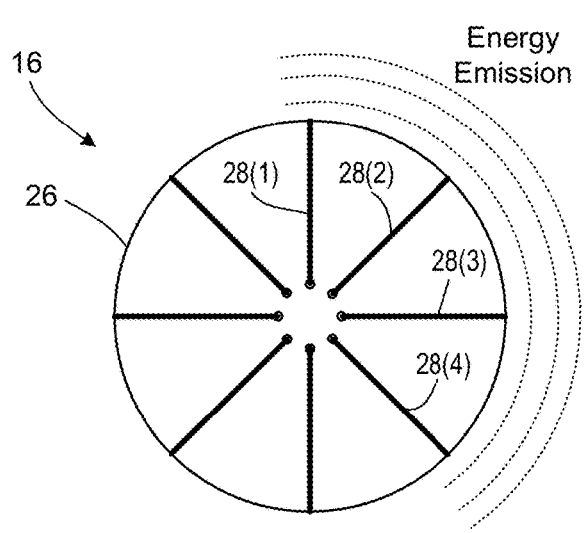

FIG. 7A is a top view of the device controller 19 with inputs 50 in a second mode and FIG. 7B is a front view of the ablation device tip illustrating the electrode array operating in the second mode. As shown, inputs 50(1)-50(4) are selected and, in turn, the corresponding conductive wires 28(1)-28(4) are activated, such that the electrode array may operate in a bipolar mode, where pairs of conductive wires 28(1)-28(2) and 28(3)-28(4) are activated.

FIGS. 8A-8E are perspective views of a distal tip 16 of the ablation device of FIG. 1 illustrating various electrode array configurations. In addition, while the conductive wires 28 have been described as extending along an external surface of the distal tip 16 in a direction that is parallel to the longitudinal axis of the device (as shown in a longitudinal configuration of conductive wires 28a in FIG. 8A), other configurations are possible. For example, one or more conductive wires 28b could extend along the external surface of the distal tip 16 in a direction that is perpendicular to the longitudinal axis of the device (as shown in a circumferential configuration in FIG. 8B). In other examples, one or more conductive wires 28c can extend from along the external surface of the distal tip 16 at an angle (e.g., non-parallel to the longitudinal axis of the device), as shown in an angled configuration in FIG. 8C. One or more conductive wires 28d, 28e, and 28f can also form a pattern along the external surface in which the conductive wires extend in various directions, as shown in a combined configuration in FIG. 8D. Additionally or alternatively, one or more conductive wires 28g can extend a reduced length of the external surface an alternative configuration in FIG. 8E.

Figure 9:
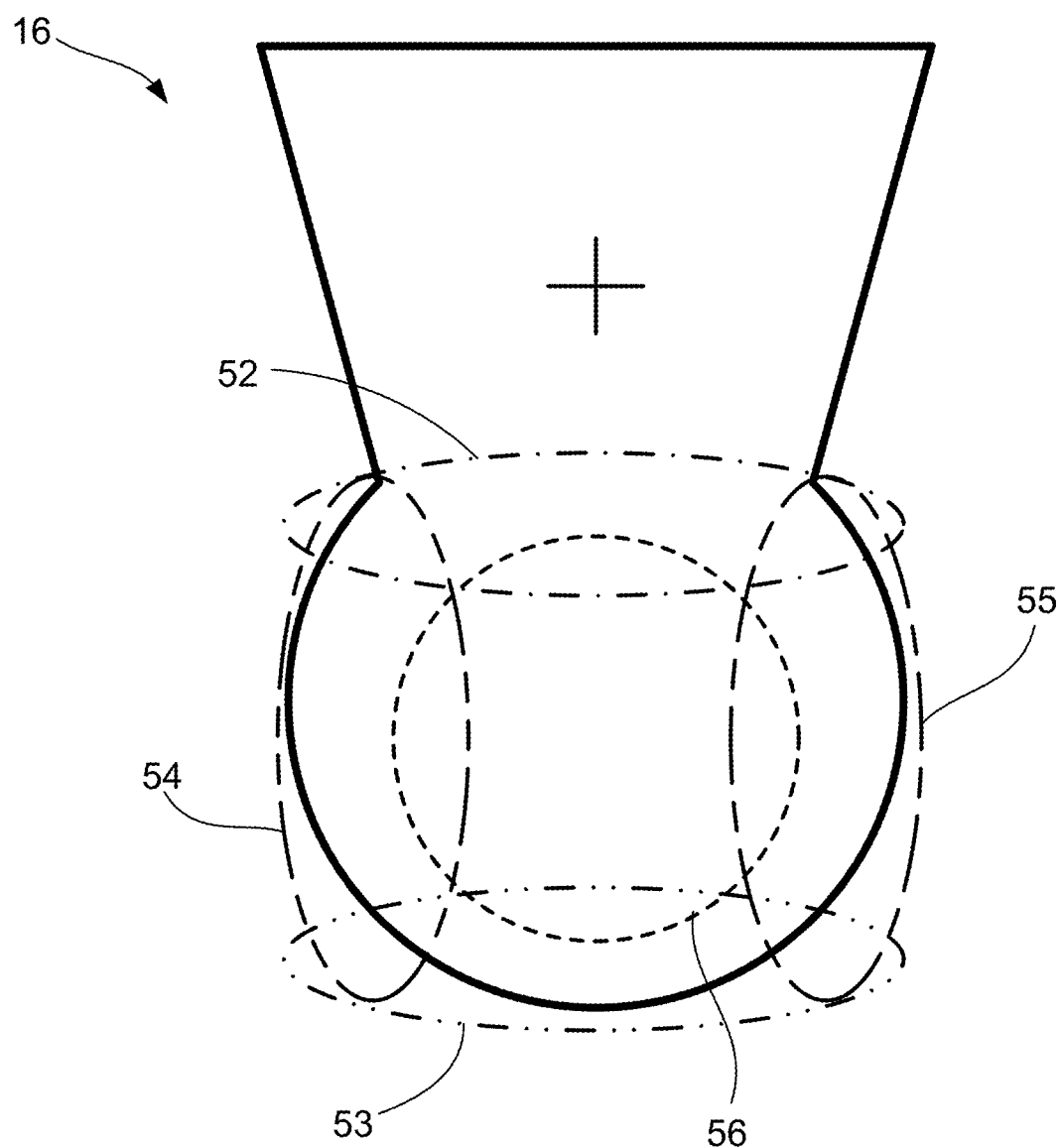
FIG. 9 is a side view of the distal tip of the ablation device of FIG. 1 including several clinical axes or sides. Each clinical axis or side includes one or more independently connected electrodes, which enables differential function and current independent drives and/or measurements.

While various conductive wires 28 have generally been described such that individual conductive members are energized or that the desired combination of conductive members is energized for a pre-selected or desired duration, in some cases, the desired combination of conductive members can be based on desired contact region of the distal tip 16. FIG. 9 is a side view of the distal tip 16 of the ablation device 14 of FIG. 1 including several clinical axes or sides. Each clinical axis or side includes one or more independently connected electrodes, which enables differential function and current independent drives and/or measurements. For example, referring to FIG. 9, the distal tip 16 can be divided into clinical axes or sides 52, 53, 54, 55, 56, and 57 (not shown). In other words, the distal tip 16 may include six clinical axes or sides of the distal portion (e.g., four sides or quadrants around spheroid body 54, 55, 56, and 57, and a bottom axis/side 52, and a top axis/side 53).

Figure 10A:
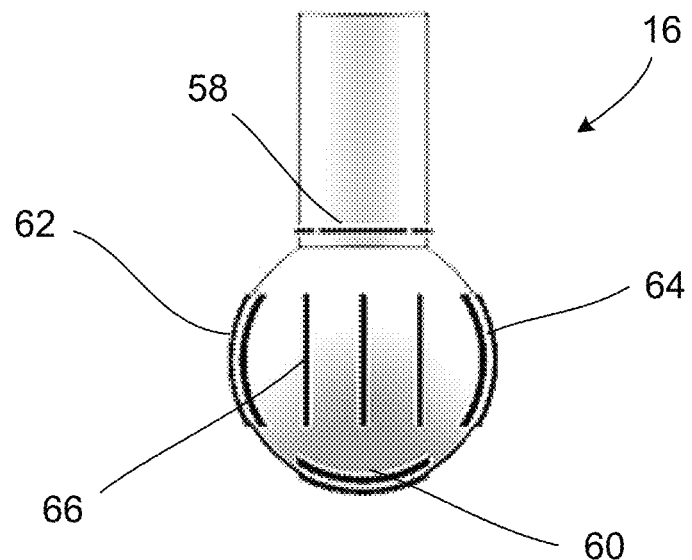
FIGS. 10A, 10B, 10C, and 10D are side and perspective views of the distal tip of the application device illustrating the different clinical axes or sides of FIG. 9.
Figure 10B:
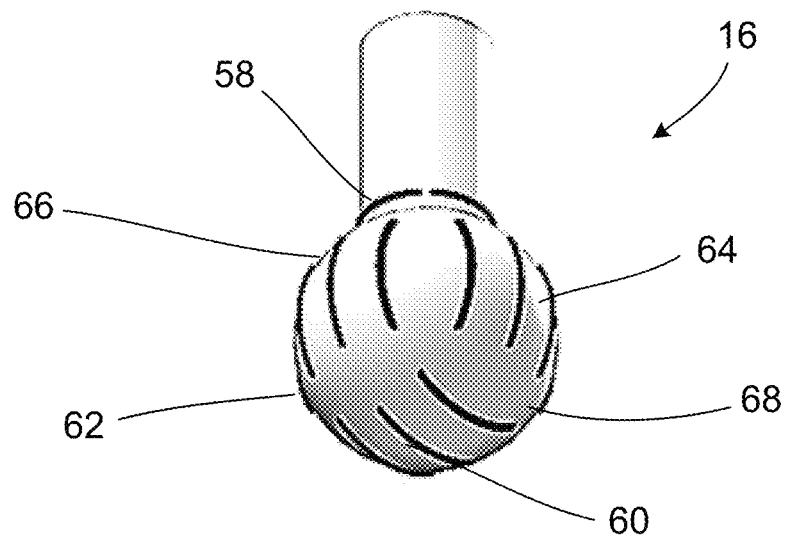
Figure 10C:
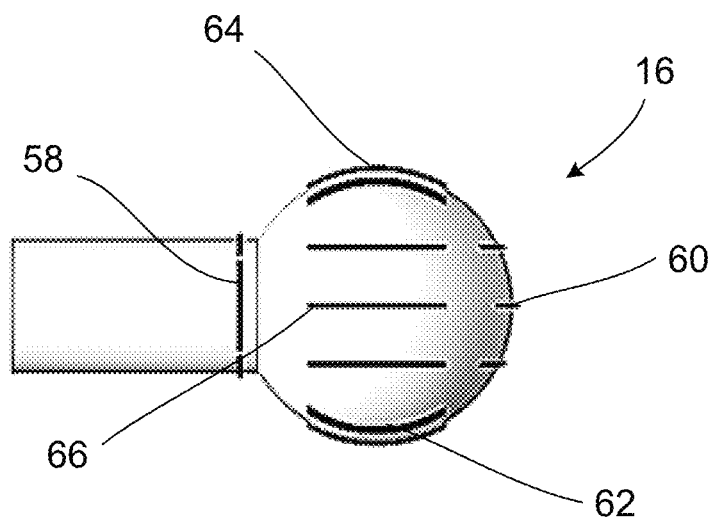
Figure 10D:
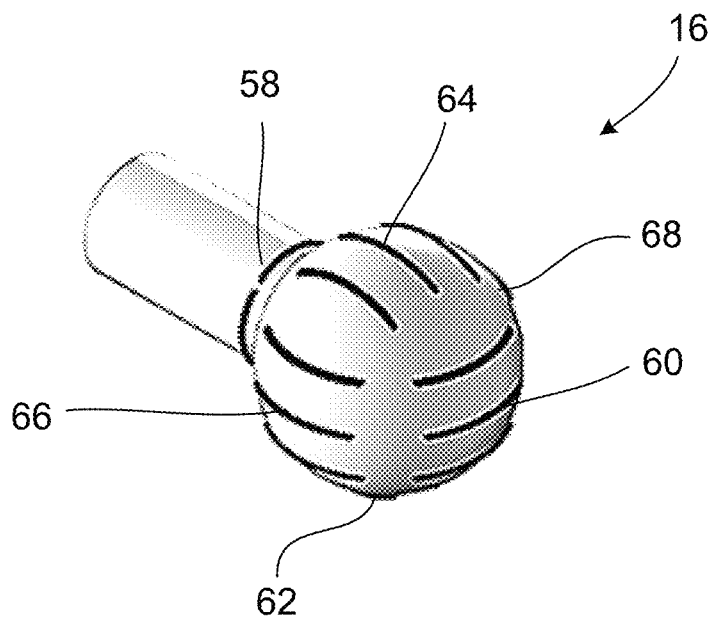

FIGS. 10-10D are side and perspective views of the distal tip of the application device illustrating the different clinical axes or sides of FIG. 9. As shown in FIGS. 10A-10D, each clinical axis can include multiple independently connected conductive wires. For example, clinical axis/side 52 can include three independently connected conductive wires 58, clinical axis/side 53 can include three independently connected conductive wires 60, clinical axis/side 54 can include three independently controlled conductive wires 62, clinical axis/side 55 can include three independently connected conductive wires 64, clinical axis/side 56 can include three independently controlled conductive wires 66, and clinical axis/side 57 can include three independently controlled conductive wires 68. The independently connected conductive wires within each clinical axis or side allows for differential function and independent energy delivery and/or measurements. While FIGS. 10A-10D generally show three conductive wires for each clinical axis or side, other combinations are possible. For example, each of the clinical axes or sides can include a combination of conductive wires ranging from one conductive wire to ten or more conductive members.

Figure 11A:
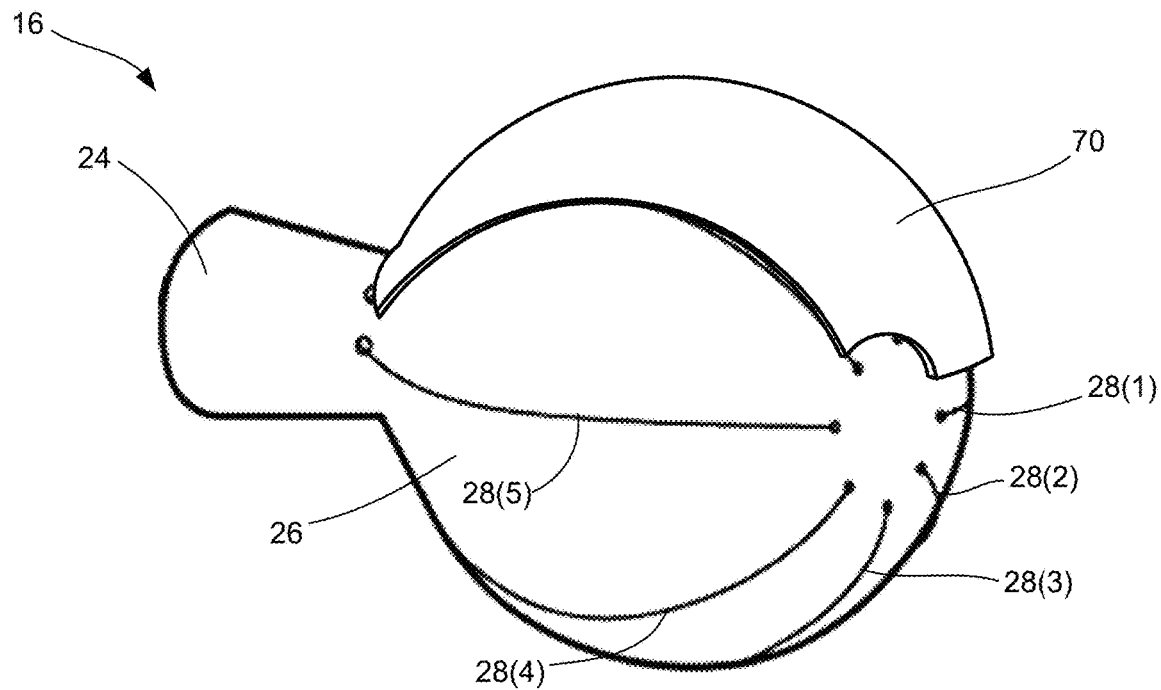
FIG. 11A is a perspective view of a distal tip of an application device consistent with the present disclosure illustrating a nonconductive cap member coupled to the distal tip and configured to block emission of energy from at least one of the conductive wires.

FIG. 11A is a perspective view of a distal tip 16 of an application device consistent with the present disclosure illustrating a nonconductive cap member 70 coupled to the distal tip 16 and configured to block emission of energy from at least one of the conductive wires 28. The nonconductive cap member 70 may be selectively positionable over one or more portions of the electrode array so as to block emission of energy therefrom while permitting the emission of energy from remaining portions of the electrode array. Accordingly, the nonconductive cap member 70 allows for the ablation of a target tissue in a specific pattern, as dictated by the physical coverage of the cap member 70.

Figure 11B:
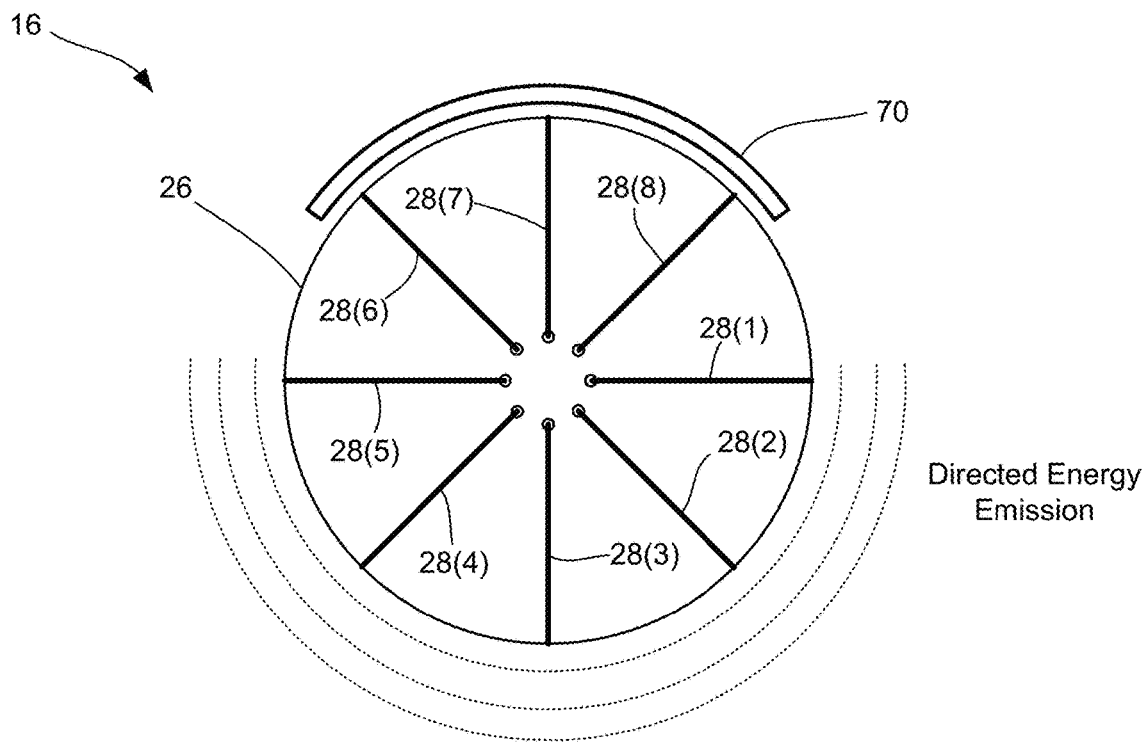
FIG. 11B is a front view of the distal tip of FIG. 11A illustrating energy emission from the distal tip in a specific pattern as dictated by the blockage of energy emission by the nonconductive cap member.
Figure 11C:
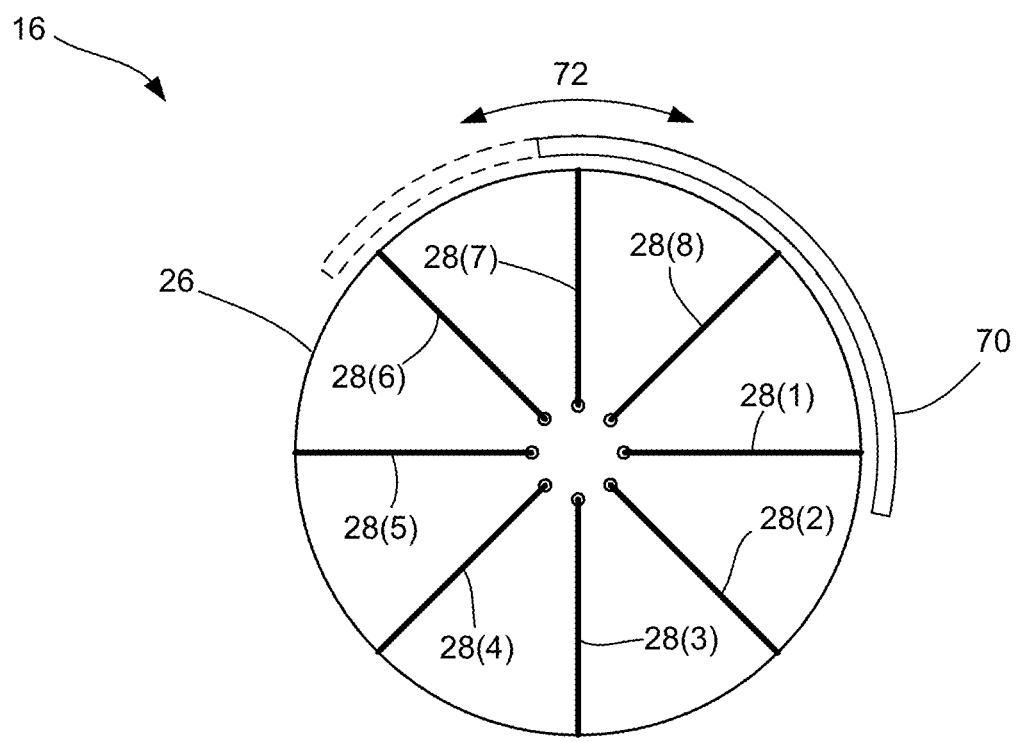
FIG. 11C is a front view of the distal tip of FIG. 11A illustrating rotational movement of the nonconductive cap member.

As shown in FIGS. 11A and 11B, the cap member 70 may be positioned over at least three of the eight conductive wires (covering conductive wires 28(6)-28(8)). Thus, by blocking energy emission from wires 28(6)-28(8), the remaining conductive wires (28(1)-28(5) remain able to emit energy in a particular ablation shape or geometry. Accordingly, the nonconductive cap member 70 may be selectively positionable over one or more of the plurality of conductive wires so as to block emission of energy from such wires and preventing emission from the corresponding portion of the electrode array, while permitting the remaining wires to emit energy. As illustrated in FIG. 11C, the cap member 70 is configured to be selectively positionable relative to the conductive wires 28. In particular, the cap member 70 may be rotationally coupled to the distal tip 16, such that a user may simply use a controller, or other means, for rotating the cap member 70 about the spheroid body 26, as indicated by arrow 72, so as to manually cover a specific wires 28 so as to select a desired ablation shape or geometry.

In some embodiments, the nonconductive cap member 70 may have a predefined shaped or size, such that the cap member 70 has a fixed area of coverage (e.g., is limited covering a specific number of conductive wires or number of electrode array portions). For example, the cap member 70 may be shaped or sized to cover a single quadrant of a spheroid distal portion, such that, at any given time, three out of four quadrants will remain uncovered and thus emit RF energy in a corresponding pattern. In other embodiments, the nonconductive cap member 70 may be shaped or sized to cover more than one quadrant (e.g., at least two quadrants, at least three quadrants, etc.).

Figure 12:
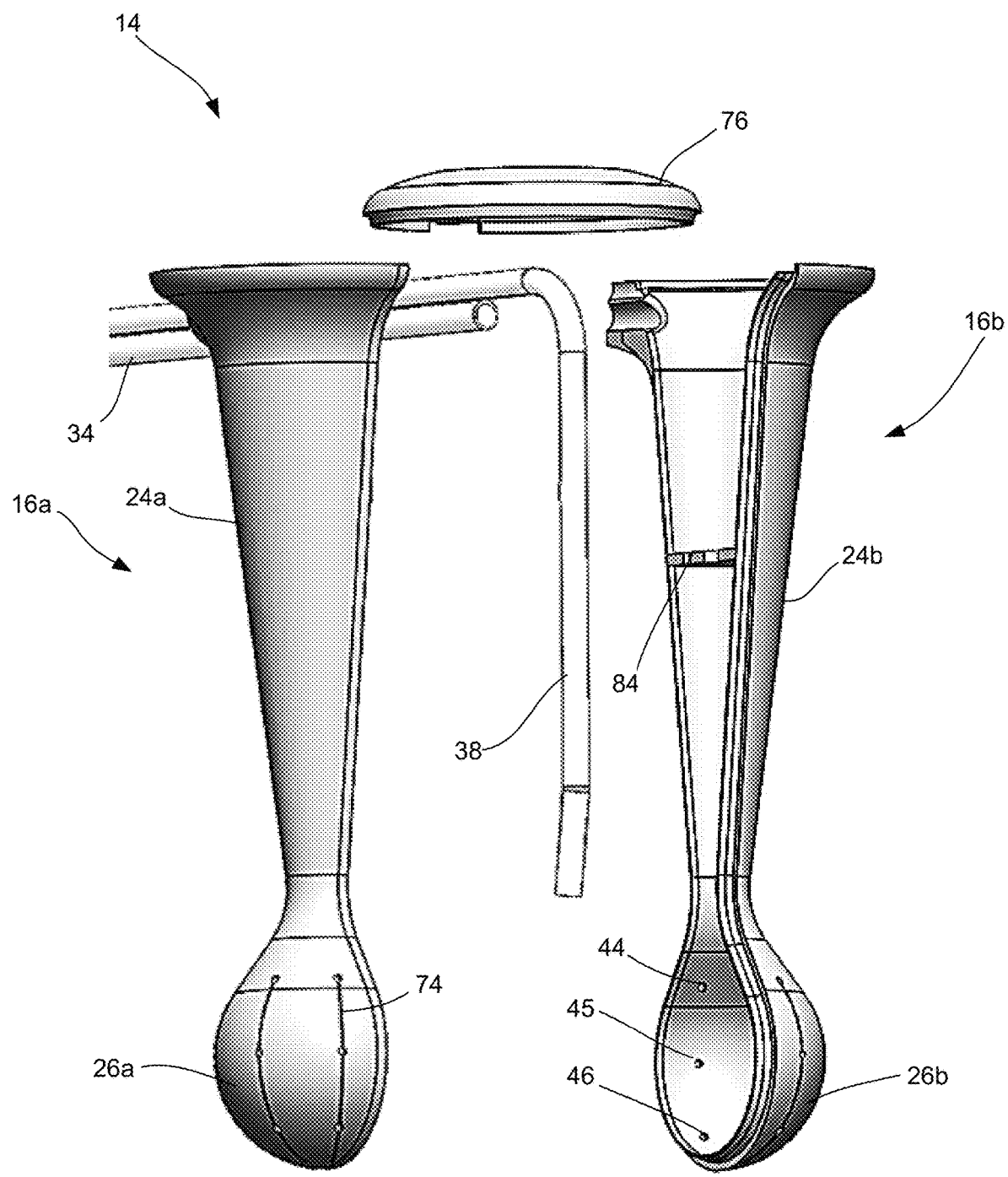
FIG. 12 is an exploded perspective view of an ablation device consistent with the present disclosure.

FIG. 12 is an exploded perspective view of an ablation device 14 consistent with the present disclosure. In some implementations, the ablation device 14, specifically the distal tip 16, may be formed from two or more pieces (tip halves 16a and 16b) configured to be coupled to one another to form the unitary distal tip 16. Each half 16a and 16b includes cooperating neck portions 24a, 24b and spheroid bodies 26a, 26b, as well as a cap 76 to be coupled to both halves 16a and 16b so as to fully enclose the interior of the distal tip 16. As further illustrated, an electrical line 34 may be provided for coupling the conductive wires 28 to the controller 18 and ablation generator 20 and a fluid line 38 may be provided for providing a fluid connection between the irrigation pump or drip 22 to the distal tip 16 so as to provide a conductive fluid (e.g., saline) to the tip 16. The electrical line 34 and/or the fluid delivery line 38 can be supported by a stabilizing element 84 within the device lumen. In some cases, the stabilizing element 84 may be integral with the neck 24 of the distal tip 16.

As previously described, conductive members 28 extend through a first port (e.g., the distal port 44), run along an external surface of the spheroid body 26 (e.g. within the groove 74) before re-entering the lumen of the distal tip 16 through another port (e.g., the proximal port 46). As will be described in greater detail herein, a conductive fluid, such as saline, may be provided to the distal tip 16 via the fluid line 38, wherein the saline may be distributed through the ports (e.g., to the distal ports 44, the proximal ports 46, and/or medial ports 45). The saline weeping through the ports and to an outer surface of the distal tip 16 is able to carry electrical current from electrode array, such that energy is transmitted from the electrode array to the tissue by way of the saline weeping from the ports, thereby creating a virtual electrode. Accordingly, upon the fluid weeping through the ports, a pool or thin film of fluid is formed on the exterior surface of the distal tip 16 and is configured to ablate surrounding tissue via the electrical current carried from the electrode array.

FIG. 13A is a front view of one embodiment of a distal tip 16 of the ablation device 14 of FIG. 12 illustrating one or more chambers formed within the distal tip 16 and FIG. 13B is a sectional view of distal tip 16 taken along lines A-A. The distal tip 16 may include at least two internal chambers configured to receive and retain fluid therein as provided by the fluid line 38. As shown in FIG. 13A, the distal tip 16 is partioned into quadrants such that it includes four separate chambers 86(1)-86(4). FIG. 13B illustrates at least two of the internal chambers 86(3) and 86(4). As shown, each chamber 86 generally includes an inlet port 88 configured to receive the fluid from the fluid delivery line 38 and further allow the fluid to flow into the corresponding chamber 86. Each chamber 86 further includes one or more perforations in a wall of the chamber. As shown in FIG. 13B, the one or more perforations may include ports 44-46. However, in some embodiments, each chamber may include additional perforations (such as perforations 98 shown in FIG. 15). The ports, or perforations, may generally be configured to allow fluid to pass therethrough, or weep, from the chamber 86 to an external surface of the spheroid body 26.

As previously described, the ablation device further includes an electrode array positioned along an external surface of the distal portion. Upon positioning the distal portion within a target site (e.g., tissue cavity to be ablated), the electrode array can be activated. The fluid weeping through the perforations of the internal chambers and to the outer surface of the spheroid body of the distal portion is a conductive fluid (e.g., saline) and thus able to carry electrical current from electrode array, such that energy is transmitted from the electrode array to the tissue by way of the fluid weeping from the perforations, thereby creating a virtual electrode.

The ablation device 14 may further include includes at least one flow control member associated with each chamber 86 so as to modify fluid flow into or out of each chamber 86 by way of a user manipulating a controller 90. The at least one flow control member is configured to transition between open, closed, and intermediate positions so as to ultimately control the passage of fluid through the one or more perforations to the external surface of the spheroid body, thereby effectively controlling the ablation pattern or shape. In particular, in the event that a flow control member associated with a first internal chamber is completely closed, thereby preventing flow of fluid through the perforations of the first internal chamber, ablation is prevented from occurring along an external surface of the spheroid body associated with the first internal chamber. Alternatively, in the event that the flow control member associated with the first internal chamber is completely opened, thereby allowing flow weeping of fluid through the perforations, ablation is allowed to occur along the external surface of the spheroid body associated with the first internal chamber. Accordingly, a user may manually manipulate each flow control member of the internal chambers so as to control the ablation shape or geometry.

Figure 14A:
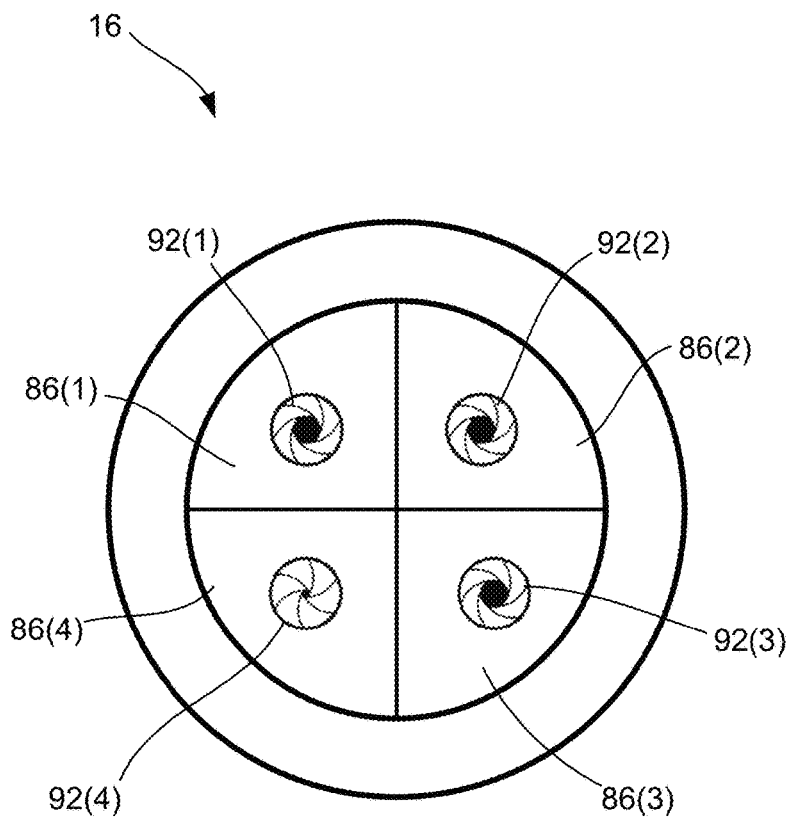
FIG. 14A is a rear view of the distal tip, in a direction from the neck towards the spheroid body, providing a view into the cavity of the distal tip and further illustrating a contractable/expandable aperture for each chamber to control passage of fluid therethrough.

As shown in FIG. 14A, the flow control member may include a contractable/expandable aperture 92 essentially serving as the inlet port for each chamber 86. FIG. 14A is a rear view of the distal tip 16, in a direction from the neck 24 towards the spheroid body 26, providing a view into the lumen 42 of the distal tip 16. As shown, each internal chamber 86(1)-86(4) has an associated contractable/expandable aperture 92(1)-92(4) configured to control the flow rate of fluid into the associated chamber 86 so as to modify fluid flow out of the ports or perforations of the chamber 86. The contractable/expandable apertures 92(1)-92(4) may generally resemble a lens iris (commonly found in cameras) configured to transition between fully open, fully closed, and intermediate positions there between.

Figure 14B:
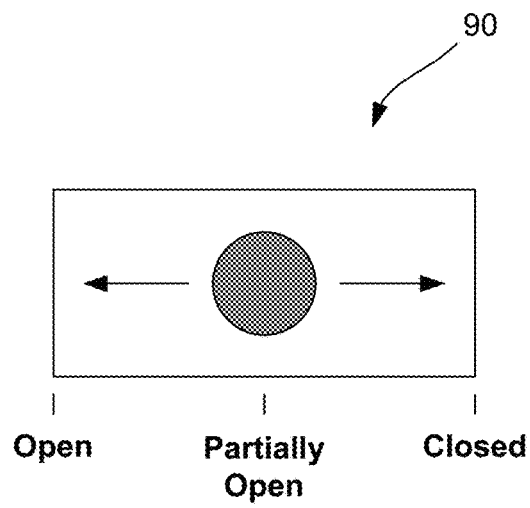
FIG. 14B illustrates an exemplary control member coupled to one of the contractable/expandable apertures and configured to control contraction/expansion of the aperture.

FIG. 14B illustrates an exemplary control member 90 coupled to a contractable/expandable aperture 92 and configured to control contraction/expansion of the aperture 92. As shown, a user may be able to manipulate the control member 90 so as to transition the aperture 92 between fully open and fully closed positions. Each aperture 92 may include an associated control member 90, such that a user may be able to independently control the contract/expansion of the individual apertures 92 separately from one another to customize the ablation shape or geometry.

Figure 15:
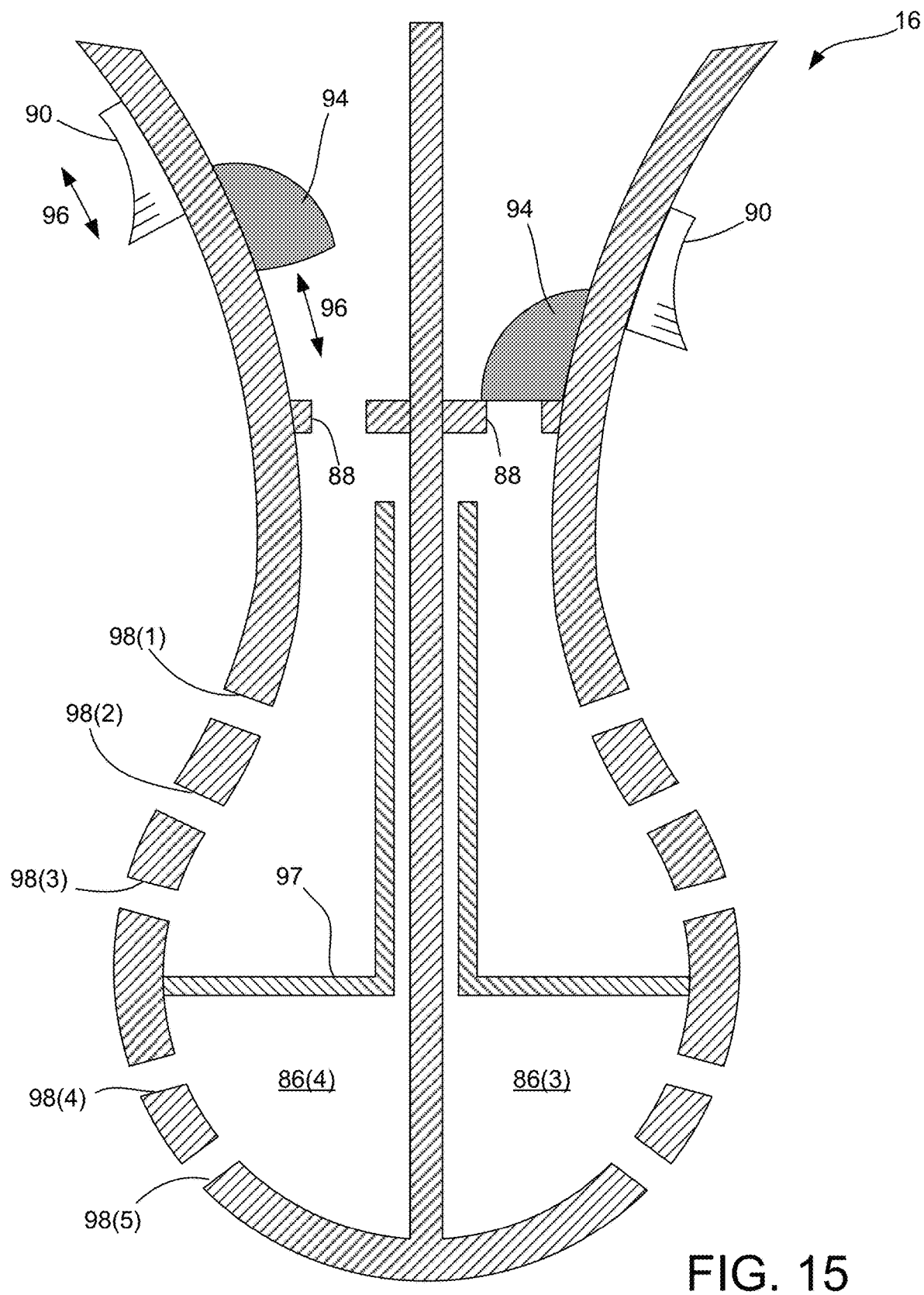
FIG. 15 is a sectional view of the ablation device of FIG. 12 illustrating a moveable plunger within each chamber and configured to move relative to the inlet port so as to allow control of passage of fluid into the inlet port and subsequent passage of fluid through one or more perforations in a chamber and to an external surface of the distal tip.

As shown in FIG. 15, the flow control member may include a moveable plunger 94 positioned within each chamber 86 and configured to move relative to the inlet port 88 so as to control of the passage of fluid into the inlet port and subsequently control weeping of fluid through the ports or perforations. As shown, each plunger 94 may be coupled a control member 90 (e.g., button, switch, etc.) configured to move in a direction relative to the inlet port 88, as indicated by arrow 96. A user may manipulate the control member 90 to move the plunger between a fully open position, as shown with respect to the inlet port of chamber 86(4), and a fully closed position, in which the plunger 94 is engaged with the inlet port 88, as shown with respect to chamber 86(3), so as to prevent fluid flow into the 86(3), thus modifying flow passage through the perforations 98.

Each of the internal chambers 86 may further include a ledge or shelf 97 provided therein, wherein the ledge 97 is positioned so as to improve uniformity of fluid distribution to one or more of the perforations, most notably the perforations most proximate to the neck 24 (e.g., perforations 98(1)-98(3). In some instances, fluid within a chamber 86 may have the tendency to pool near a bottom of the chamber 86 depending on the orientation of the spheroid body 26 due to gravity. Thus, those perforations that are closest to the neck 24 will likely not receive fluid to pass therethrough, which may lead to inaccurate or incomplete ablation, as the fluid is not evenly distributed along the external surface of the body 26. The ledge 97 is positioned in such a manner that fluid may first accumulate within a portion of the ledge 97 and allow the perforations 98(1)-98(3) to fill with fluid prior to the remaining perforations 98(4) and 98(5), which will normally fill with fluid, thereby ensuring uniform distribution of fluid weeping.

FIGS. 16 and 17 are perspective and exploded perspective views, respectively, of another one embodiment of a device controller 200 consistent with the present disclosure. Similar to user switch or interface 19, the device controller 200 may serve as the device controller 18 and is in electrical communication with the ablation generator 20 as well as the irrigation pump/drip 22. Accordingly, the controller 200 can provide a user with various options with respect to controlling the ablation output of an ablation device consistent with the present disclosure, specifically providing a surgeon with the functions provided by switch 19 and/or the controller 18 having control of the CAS system 100. For example, controller 200 may include the CAS system 100 configured to provide custom ablation shaping controls for a user to create custom, user-defined ablation geometries or profiles, as well as control particular ablation parameters, such as control of timing of the emission (e.g., length of time, intervals, etc.) as well as the depth of RF energy penetration.

As shown, the controller 200 may include a first halve or shell 202a and a second halve or shell 202b for housing a PC 204 within, the PC board 204 comprising circuitry and hardware for controlling various parameters of the device 14 during an ablation procedure. The controller 200 further includes a display 206, such as an LCD or LED display for providing a visual representation of one or more parameters associated with the device 14, including, but not limited to, device status (e.g., power on/off, ablation on/off, fluid delivery on/off) as well as one or more parameters associated with the RF ablation (e.g., energy output, elapsed time, timer, temperature, conductivity, etc.). The controller 200 may further include a top membrane 208 affixed over the PC board 204 and configured to provide user input (by way of buttons or other controls) with which a user (e.g., surgeon or medical professional) may interact with a user interface provided on the display 206. The controller 200 may be configured to control at least the amount of electrical current applied to one or more of the conductive wires 28 from the ablation generator 20 and the amount of fluid to be delivered to the device 14 from the irrigation pump/drip 22.

Figure 18:
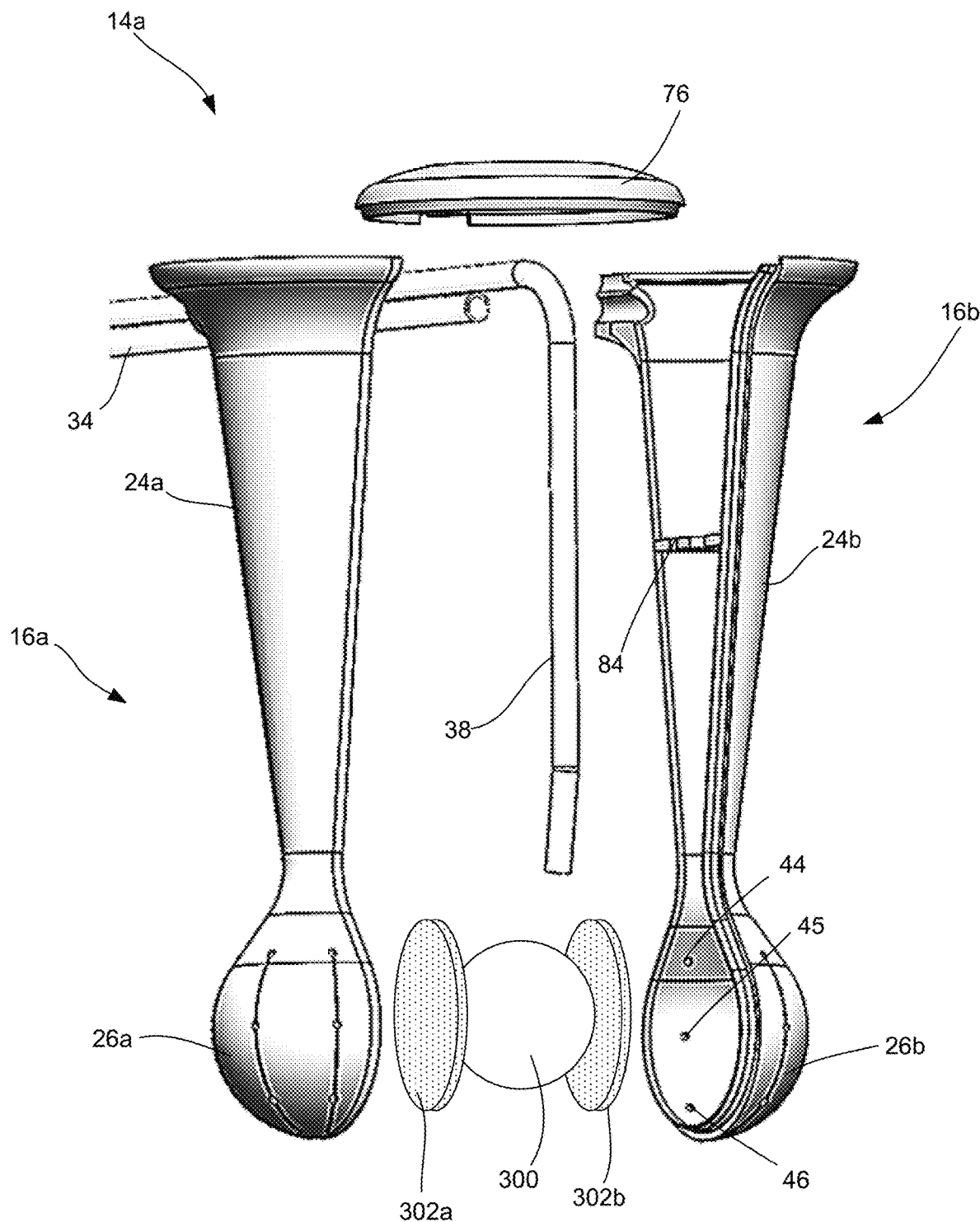
FIG. 18 is an exploded perspective view of another embodiment of an ablation device consistent with the present disclosure.

FIG. 18 is an exploded perspective view of another embodiment of an ablation device 14a consistent with the present disclosure. The device 14a is similarly configured as device 14 illustrated in FIG. 12, and includes similar elements. For example, the device 14a includes the distal tip 16 formed from two or more pieces (tip halves 16a and 16b) configured to be coupled to one another to form the unitary distal tip 16. Each half 16a and 16b includes cooperating neck portions 24a, 24b and spheroid bodies 26a, 26b, as well as a cap 76 to be coupled to both halves 16a and 16b so as to fully enclose the interior of the distal tip 16. As further illustrated, an electrical line 34 may be provided for coupling the conductive wires 28 to the controller 18 (or controller 200) and ablation generator 20 and a fluid line 38 may be provided for providing a fluid connection between the irrigation pump or drip 22 to the distal tip 16 so as to provide a conductive fluid (e.g., saline) to the tip 16.

The device 14a is configured to provide RF ablation via a virtual electrode arrangement, which includes distribution of a fluid along an exterior surface of the distal tip 16 and, upon activation of the electrode array, the fluid may carry, or otherwise promote, energy emitted from the electrode array to the surrounding tissue. For example, the nonconductive spheroid body 26 includes an interior chamber (when the first and second halves 26a, 26b are coupled to one another) for retaining at least a spacing member 300 (also referred to herein as "spacer ball") and one or more hydrophilic inserts 302a, 302b surrounding the spacing member 300. The interior chamber of the distal tip 16 is configured to receive and retain a fluid (e.g., saline) therein from a fluid source. The hydrophilic inserts 302a, 302b are configured receive and evenly distribute the fluid through the distal tip 16 by wicking the saline against gravity. The hydrophilic inserts 302a and 302b can be formed from a hydrophilic foam material (e.g., hydrophilic polyurethane).

As previously described, the distal tip 16 may generally include a plurality of ports or apertures configured to allow the fluid to pass therethrough, or weep, from the interior chamber to an external surface of the distal tip 16. Accordingly, in some embodiments, all of the ports (e.g., proximal ports 44, medial ports 45, and distal ports 46) may be configured to allow for passage of fluid from the inserts 302a, 302b to the exterior surface of the distal tip 16. However, in some embodiments, only the medial ports 45 may allow for fluid passage, while the proximal and distal ports 44, 46 may be blocked via a heat shrink or other occlusive material.

The spacer member 300 may formed from a nonconductive material and may be shaped and sized so as to maintain the hydrophilic inserts 302a, 302b in sufficient contact with the interior surface of the distal tip wall, and specifically in contact with the one or more ports, such that the hydrophilic inserts 302a, 302b provides uniformity of saline distribution to the ports. In some embodiments, the spacer member 300 may have a generally spherical body, corresponding to the interior contour of the chamber of the spheroid body 26.

Accordingly, upon positioning the distal tip 16 within a target site (e.g., tissue cavity to be ablated), the electrode array can be activated and fluid delivery can be initiated. The fluid weeping through the ports to the exterior surface of the distal tip is able to carry energy from electrode array, thereby creating a virtual electrode. Accordingly, upon the fluid weeping through the port, a pool or thin film of fluid is formed on the exterior surface of the distal portion and is configured to ablate surrounding tissue via the RF energy carried from the electrode array.

Figure 19:
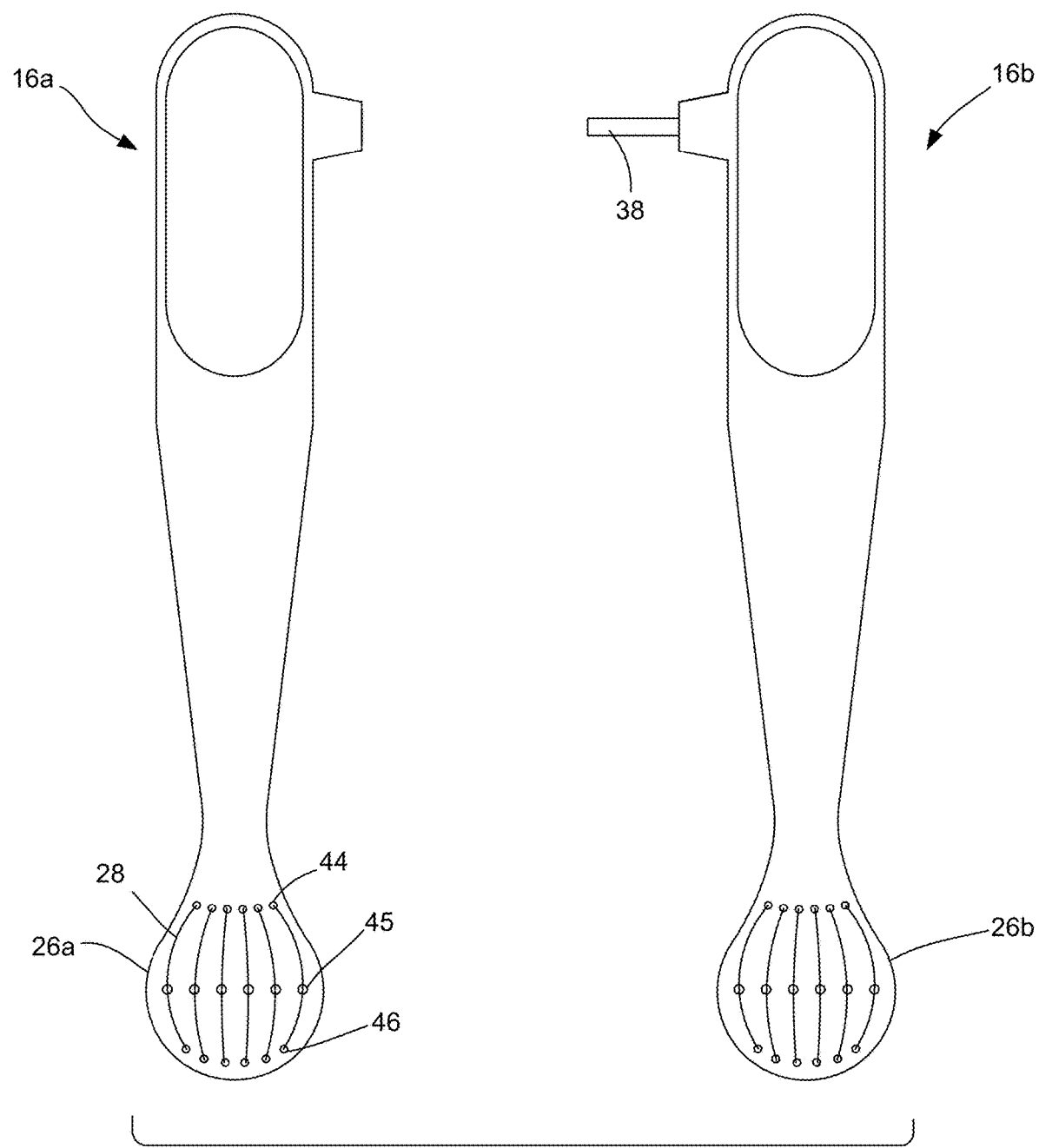
FIG. 19 is a plan view of the ablation device of FIG. 18 illustrating the two halves of the device separated from one another and showing the external surface of each.
Figure 20:
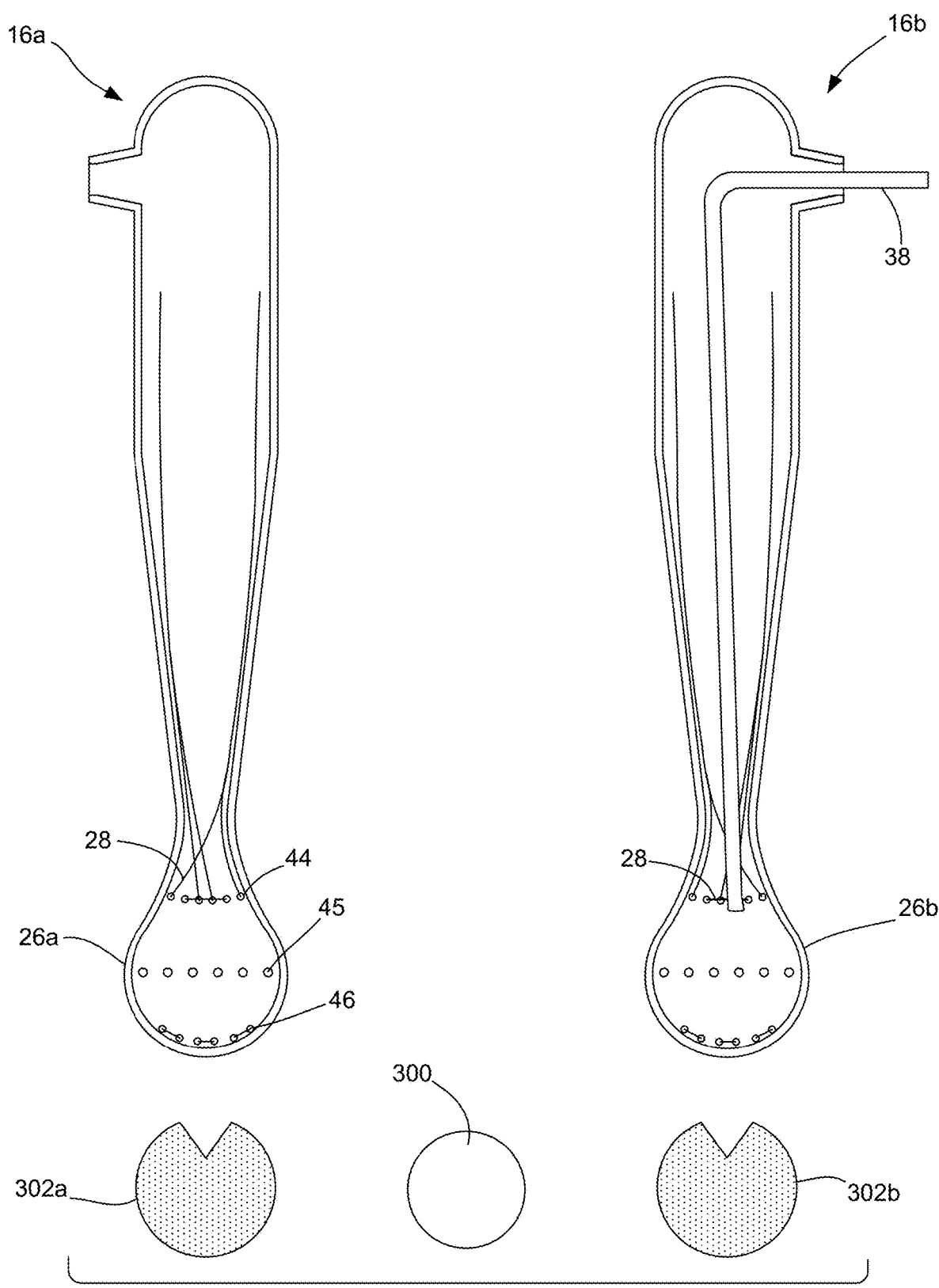
FIG. 20 is a plan view of the ablation device of FIG. 18 illustrating the two halves of the device separated from one another and showing the interior surface of each.

As previously described herein, conductive wires 28 may generally extend through a first port (e.g., the distal port 44), run along an external surface of the spheroid body 26 before re-entering the lumen of the distal tip 16 through another port (e.g., the proximal port 46). FIGS. 19, 20, 21A-21B, and 22A-22B illustrate another arrangement of conductive wires 28, in which at least four different conductive wires are provided, two of which serve as supply electrodes and the other two serve as return electrodes. Each of the four different conductive wires generally pass through at least two different proximal ports and two different distal ports, while remaining isolated from one another. FIG. 19 is a plan view of the ablation device 14a illustrating the two halves of the device tip 16a, 16b separated from one another and showing the external surface each, while FIG. 20 shows the interior surface of each.

FIGS. 21A and 21B are enlarged views of the spheroid body of the first halve 16a of the device 14a showing the exterior and interior surfaces, respectively, and further illustrating the particular arrangement of first and second conductive wires 28(1) and 28(2), partly in phantom, extending through proximal and distal ports 44, 46 of the spheroid body 26a. The following description of the first and second conductive wires 28(1) and 28(2) provides a general pathway of each wire, including passages through ports and extensions along lengths of the interior and exterior surfaces of the tip 16. In the illustrated embodiment, a first conductive wire 28(1) may serve as a return electrode while a second conductive wire 28(2) may serve as a supply electrode.

As shown, the first conductive wire 28(1) extends within the lumen of the tip 16a and passes through proximal port 44(1), extends along the exterior surface of the spheroid body 26a towards the distal ports (generally parallel to longitudinal axis of device), passes through distal port 46(1), extends along the interior surface of the body 26a towards adjacent distal ports (generally transverse to longitudinal axis of the device), passes through distal port 46(2), extends along the exterior surface of the spheroid body 26a back towards the proximal ports, passes through proximal port 44(2), extends along the interior surface of body 26a towards adjacent proximal ports, passes through proximal port 44(5), extends along the exterior surface of the spheroid body 26a back towards the distal ports, passes through distal port 46(5), extends along the interior surface of the body 26a towards adjacent distal ports, passes through distal port 46(6), extends along the exterior surface of the spheroid body 26a back towards the proximal ports, passes through proximal port 44(6), and extends back through lumen of the tip 16a. Accordingly, the first conductive wire 28(1) has at least four portions that extend along the exterior surface of the spheroid body 26a.

The second conductive wire 28(2) extends within the lumen of the tip 16a and passes through distal port 44(3), extends along the exterior surface of the spheroid body 26a towards the distal ports (generally parallel to longitudinal axis of device), passes through distal port 46(3), extends along the interior surface of the body 26a towards adjacent distal ports (generally transverse to longitudinal axis of the device), passes through distal port 46(4), extends along the exterior surface of the spheroid body 26a back towards the proximal ports, passes through proximal port 44(4), and extends back through lumen of the tip 16a. Accordingly, the second conductive wire 28(2) has at least two portions that extend along the exterior surface of the spheroid body 26a.

Figure 22B:
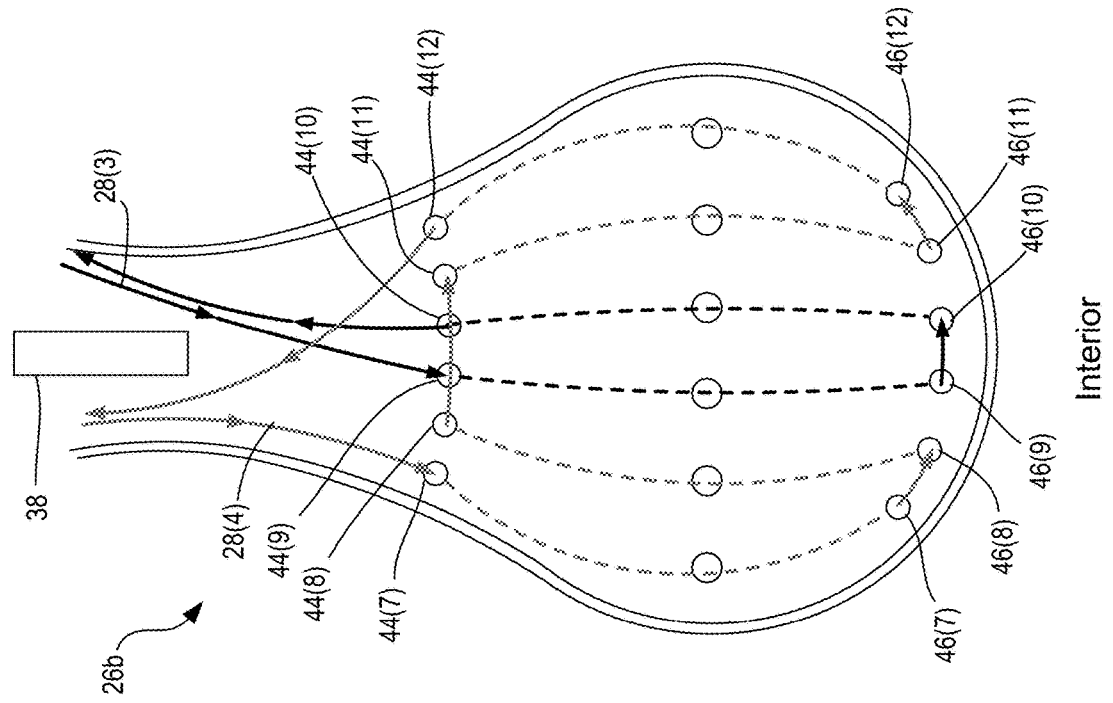
FIGS. 22A and 22B are enlarged views of the spheroid body of the second halve of the device showing the exterior and interior surfaces, respectively, and further illustrating the particular arrangement of third and fourth conductive wires extending through proximal and distal ports of the spheroid body.
Figure 22A:
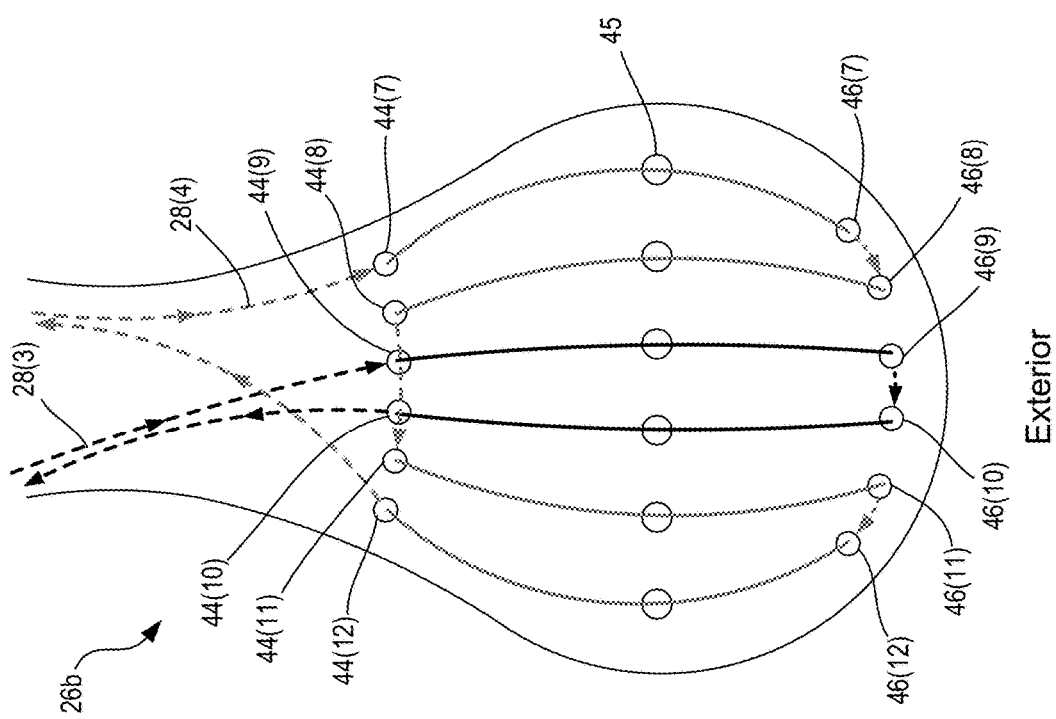

FIGS. 22A and 22B are enlarged views of the spheroid body of the second halve 16b of the device 14a showing the exterior and interior surfaces, respectively, and further illustrating the particular arrangement of third and fourth conductive wires 28(3) and 28(4) extending through proximal and distal ports of the spheroid body 26b. The following description of the third and fourth conductive wires 28(3) and 28(4) provides a general pathway of each wire, including passages through ports and extensions along lengths of the interior and exterior surfaces of the tip 16. In the illustrated embodiment, a third conductive wire 28(3) may serve as a return electrode while a second conductive wire 28(4) may serve as a supply electrode.

As shown, the third conductive wire 28(3) extends within the lumen of the tip 16a and passes through proximal port 44(9), extends along the exterior surface of the spheroid body 26b towards the distal ports (generally parallel to longitudinal axis of device), passes through distal port 46(9), extends along the interior surface of the body 26b towards adjacent distal ports (generally transverse to longitudinal axis of the device), passes through distal port 46(10), extends along the exterior surface of the spheroid body 26b back towards the proximal ports, passes through proximal port 44(10), and extends back through lumen of the tip 16a. Accordingly, the third conductive wire 28(3) has at least two portions that extend along the exterior surface of the spheroid body 26b.

The fourth conductive wire 28(4) extends within the lumen of the tip 16b and passes through proximal port 44(7), extends along the exterior surface of the spheroid body 26b towards the distal ports (generally parallel to longitudinal axis of device), passes through distal port 46(7), extends along the interior surface of the body 26b towards adjacent distal ports (generally transverse to longitudinal axis of the device), passes through distal port 46(8), extends along the exterior surface of the spheroid body 26b back towards the proximal ports, passes through proximal port 44(8), extends along the interior surface of body 26b towards adjacent proximal ports, passes through proximal port 44(11), extends along the exterior surface of the spheroid body 26b back towards the distal ports, passes through distal port 46(11), extends along the interior surface of the body 26b towards adjacent distal ports, passes through distal port 46(12), extends along the exterior surface of the spheroid body 26b back towards the proximal ports, passes through proximal port 44(12), and extends back through lumen of the tip 16a. Accordingly, the fourth conductive wire 28(4) has at least four portions that extend along the exterior surface of the spheroid body 26b.

Furthermore, each of the four conductive wires 28(1)-28(4) remain electrically isolated and independent from one another such that, each, or one or more sets of a combination of, the conductive wires, can independently receive an electrical current from the ablation generator and independently conduct energy, the energy including RF energy. This allows energy to be selectively delivered to a designated conductive wire or combination of conductive wires. This design also enables the ablation device to function in a bipolar mode because a first conductive wire (or combination of conductive wires) can deliver energy to the surrounding tissue through its electrical connection with an ablation generator while a second conductive wire (or combination of conductive wire(s) can function as a ground or neutral conductive member.

The independent control of each wire or sets of wires allows for activation (e.g., emission of RF energy) of corresponding portions of the electrode array. For example, the electrode array may be partitioned into specific portions which may correspond to clinical axes or sides of the distal portion of the device. In one embodiment, the electrode array may include at least four distinct portions (i.e., individual or sets of conductive wires) corresponding to four clinical axes or sides of the distal portion (e.g, four sides or quadrants around spheroid body).

Figure 23:
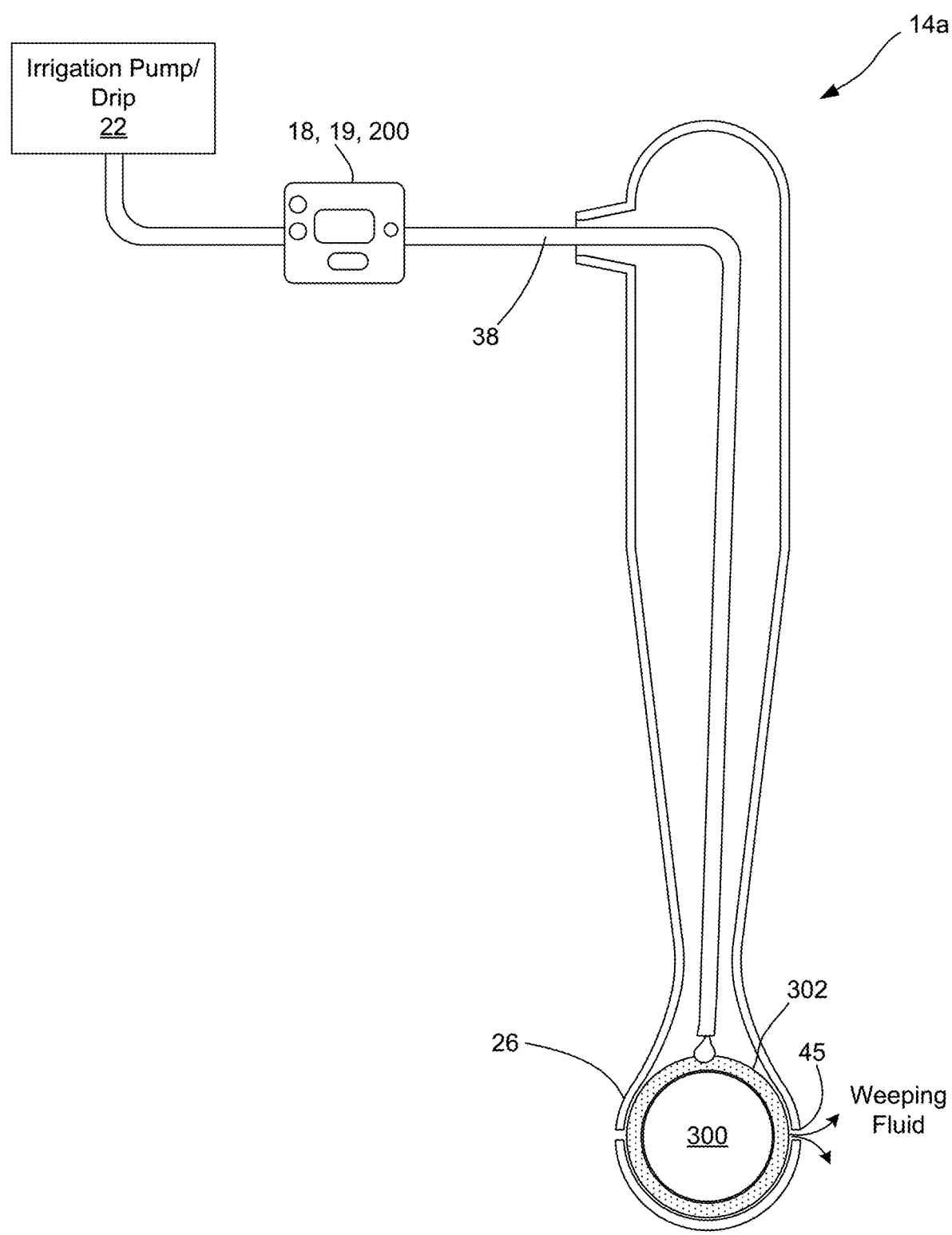
FIG. 23 is a schematic illustration of the ablation device of FIG. 18 illustrating delivery of fluid from the irrigation pump, as controlled by the controller, to the hydrophilic insert within the interior chamber of the distal portion of the device.

FIG. 23 is a schematic illustration of the ablation device 14a illustrating delivery of fluid from the irrigation pump 22, as controlled by the controller 19, to the hydrophilic inserts 302a, 302b within the interior chamber of the distal tip 16, wherein the fluid can be subsequently distributed to an exterior surface of the spheroid body 26 resulting in a virtual electrode arrangement upon activation of one or more portions of the electrode array. As shown, the saline may be distributed through at least the medial ports 45, such that the weeping saline is able to carry electrical current from electrode array, such that energy is transmitted from the electrode array to the tissue by way of the saline weeping from the ports, thereby creating a virtual electrode. Accordingly, upon the fluid weeping through the medial port, a pool or thin film of fluid is formed on the exterior surface of the spheroid body 26 and is configured to ablate surrounding tissue via the electrical current carried from the electrode array.

Figure 24:
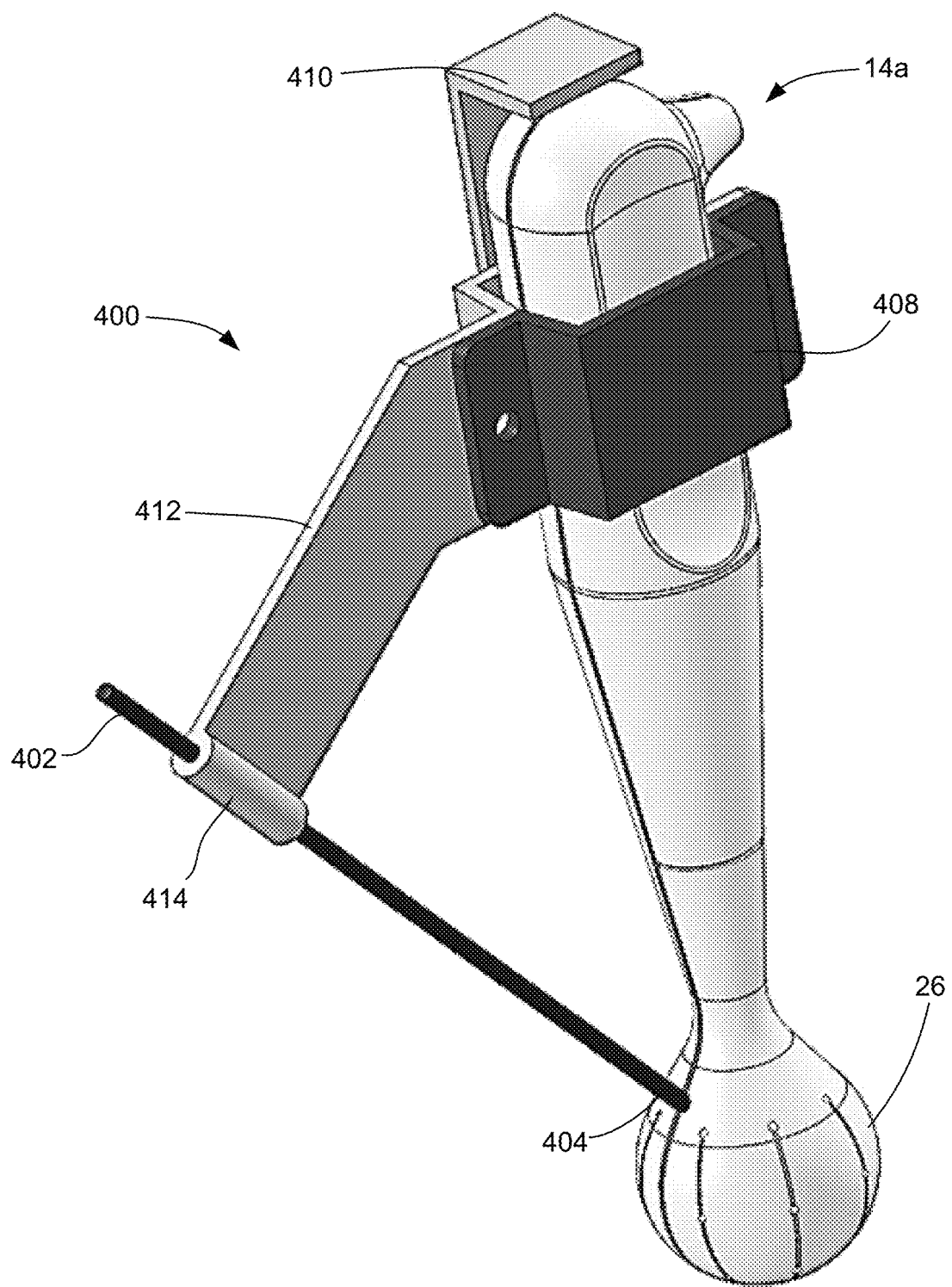
FIG. 24 is a perspective view of a detachable mount for holding a temperature probe (or any other separate monitoring device) at a desired position relative to the distal portion of the ablation device for the collection of temperature data during an RF ablation procedure.
Figure 25:
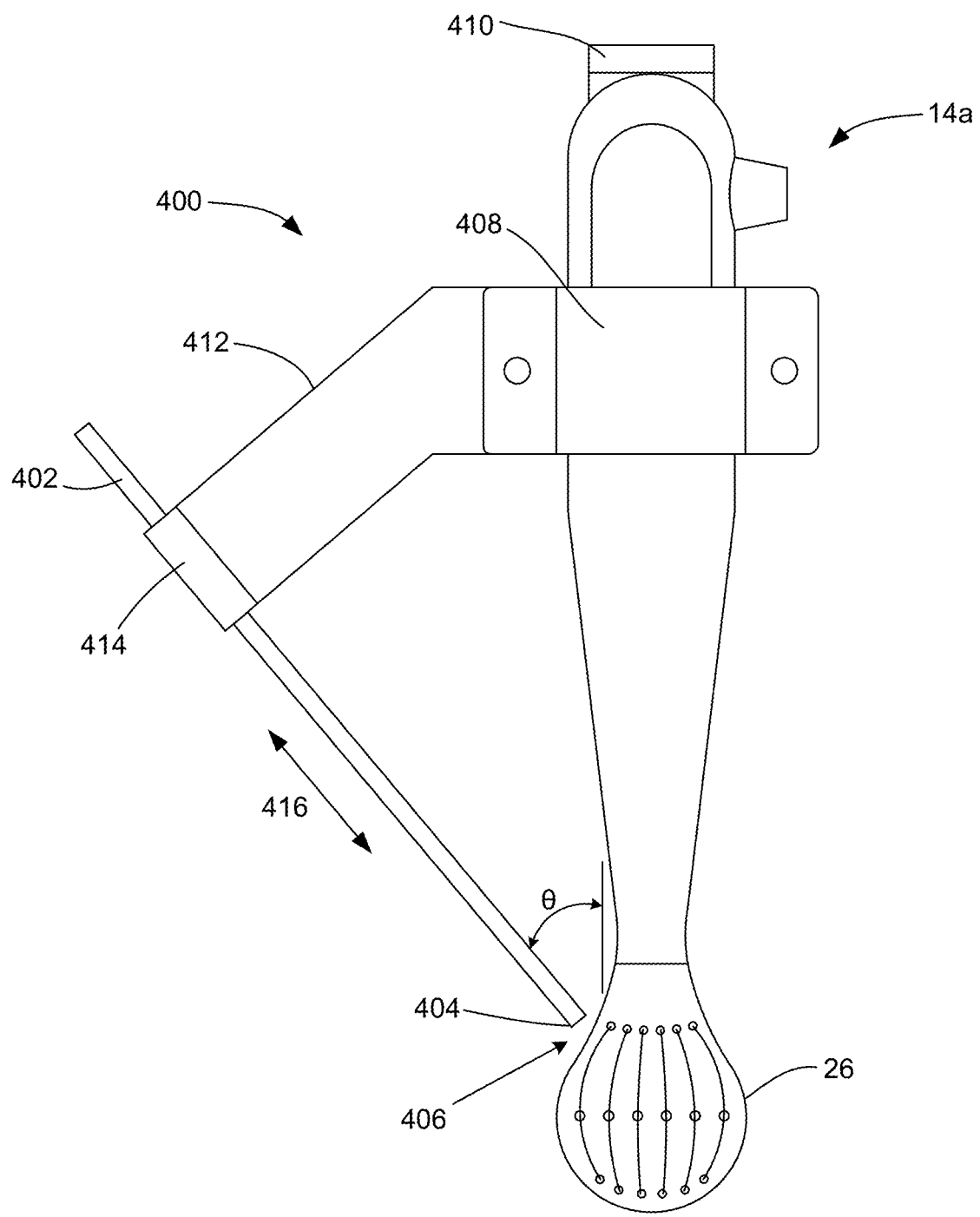
FIG. 25 is a plan view of the detachable mount holding the temperature probe relative to the distal portion of the ablation device.

FIGS. 24 and 25 are perspective and plan views of a detachable mount 400 for holding and maintaining a temperature probe 402 (or any other separate monitoring device) at a desired position, as indicated by arrow 406, relative to the spheroid body 26 of the distal tip of the ablation device 14. In particular, the mount 400 allows for an operator (e.g., surgeon) to releasably couple a temperature probe 402, or other measurement device, to the ablation device 14a and further position the working end 404 of the probe 402 in close proximity to the spheroid body 2 for the collection of temperature data during an RF ablation procedure.

As previously described herein, the controller 18 (as well as 19 or 200) may be configured to provide a surgeon with the ability to control ablation, such as controlling the supply of power to one or more conductive wires as well as control the delivery of fluid to the device tip 16. Furthermore, the controller 18 may provide device status (e.g., power on/off, ablation on/off, fluid delivery on/off) as well as one or more parameters associated with the RF ablation (e.g., energy output, elapsed time, timer, temperature, conductivity, etc.). Thus, in some instances, particularly when using the CAS system 100 described previously herein, it may be important to monitor at least the temperature adjacent to the device tip 16 during the ablation procedure, as well as pre-ablation and post-ablation, as temperature may be indicative of the status of surrounding tissue that is being, or is intended to be, ablated. Furthermore, it may be important to monitor the temperature at certain distances from the device tip 14 and at certain angles. Current devices may include a thermocouple mechanism integrated into the device. However, such configurations lack the ability to obtain temperature measurement at specific distances and angles relative to the ablation tip. The mount 400 is configured to provide a surgeon with the ability to adjacent the angle at which the temperature probe is positioned relative to the device tip 16 as well as the distance from the device tip 16, thereby overcoming the drawbacks of integrated thermocouples.

As shown, the mount 400 generally includes a body having a first end 408 configured to be releasably coupled to at least the proximal end of the device 14 by way of a clamping mechanism or latch-type engagement. The first end 408 includes a top guard member 410 configured to partially enclose at least the proximal end of the device 14, to further enhance securement of the mount 400 to the device 14. The mount 400 further includes an arm member 412 extending from the first end 408 and providing a second end 414 positioned a distance from the first end 408. The second end 414 is configured to hold the temperature probe 402 at a desired position, including a desired distance from the spheroid body 26 and a desired angle θ relative to the longitudinal axis of the ablation device. For example, in one embodiment, the second end 414 may include a bore or channel configured to receive and retain a portion of the temperature probe 402 within. The second end 414 may further allow for the temperature probe 402 to translate along the bore or channel, as indicated by arrow 416, to thereby adjust the distance of the temperature probe tip 404 relative to the spheroid body of the device tip. In some embodiments, the arm 412 and/or second end 414 may articulate relative to one another and/or the first end 408. Accordingly, the angle of the temperature probe 402 may also be adjusted as desired.

Accordingly, the system of the present invention is configured to provide a user with multiple features allowing custom ablation shaping, which includes the creation of custom, user-defined ablation geometries depending on the target site. In particular, rather than simply providing a universal RF ablation shape or profile, the system allows for a user to customize the emission of energy to a targeted portion of marginal tissue within the cavity, which is particularly useful in instances in which non-uniform ablation is desired. The customized emission of energy may include a specific shape or geometry of emission, as well as time and depth of penetration of RF energy.

The devices, systems, and methods of the present disclosure can help to ensure that all microscopic disease in the local environment has been treated. This is especially true in the treatment of tumors that have a tendency to recur. Furthermore, by providing custom ablating shaping, in which the single ablation device may provide numerous RF energy emission shapes or profiles, the system of the present invention allows for non-uniform ablation to occur. This is particularly useful in controlling ablation shape so as to avoid vital organs and any critical internal/external structures (e.g., bone, muscle, skin) in close proximity to the tumor site, while ensuring that residual marginal tissue within the local environment has been treated.

As used in any embodiment herein, the term "controller", "module", "subsystem", or the like, may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The controller or subsystem may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A system for monitoring and controlling tissue ablation, the system comprising:
   a controller configured to selectively control energy emission from an electrode array of an ablation device based on ablation feedback received from ablation energy during an ablation procedure with the ablation device, the controller comprising a hardware processor coupled to memory containing instructions executable by the processor to cause the controller to:
   receive feedback data from one or more sensors during the ablation procedure, the feedback data comprising one or more measurements associated with at least one of operation of the electrode array of the ablation device and tissue adjacent to the electrode array;
   generate an ablation pattern for controlling energy emission from the electrode array of the ablation device in response to the received feedback data; and
   continuously receive feedback data from ablation energy during the ablation procedure to continuously update the ablation pattern for controlling energy emission from the electrode array of the ablation device in response to the received feedback data.

2. The system of claim 1, wherein the measurements comprise at least one of: elapsed time during an ablation period; electrical conductivity or complex impedance associated with one or more conductive wires of the electrode array of the ablation device; electrical current supplied to the one or more conductive wires; temperature of tissue adjacent to the electrode array; photonic properties of the tissue adjacent to the electrode array; and a combination thereof.

3. The system of claim 2, the system further comprising at least one of a temperature sensor, voltage sensor, signal detector, and impedance sensor configured to obtain measurements during an ablation procedure.

4. The system of claim 2, wherein the system further comprises an ablation tracking interface module configured to receive the feedback data.

5. The system of claim 1, wherein the ablation pattern comprises at least one of: a selected one or more conductive wires, from a plurality of conductive wires of the electrode array, to receive electrical current for energy emission therefrom; a level of electrical current to be supplied to a selected one or more conductive wires; a length of elapsed time during which electrical current is to be supplied to a selected one or more conductive wires; one or more intervals over which electrical current is to be supplied to a selected one or more conductive wires; and a combination thereof.

6. The system of claim 5, wherein the electrode array of the ablation device comprises a plurality of independent conductive wires configured to independently receive electrical current.

7. The system of claim 6, wherein the ablation pattern comprises a selected one, or a selected set of two or more, of the plurality of conductive wires resulting in emission of energy therefrom corresponding to a portion of the electrode array, thereby resulting in targeted ablation of adjacent tissue.

8. The system of claim 1, wherein the generation of the ablation pattern comprises processing the feedback data in real-, or near-real-, time and generating ablation status mapping based on the processed feedback data, wherein the ablation status mapping provides an estimation of the state of the tissue to be, currently undergoing, or having undergone ablation.

9. The system of claim 8, wherein
   the controller is configured to collect data from a machine learning model and use the model to generate and update the ablation pattern.

10. The system of claim 8, wherein the generation of the ablation pattern further comprises a combination of ablation status mapping data with an electrode activation algorithm for assignment of one or more ablation control parameters for selective conductive wire activation for subsequent targeted ablation of adjacent tissue.

11. The system of claim 10, wherein the system further comprises an ablation mapping module and an ablation geometry shaping module, the ablation mapping module configured to receive and process the feedback data and transmit mapping data to the ablation geometry shaping module configured to process the mapping data to generate the ablation pattern.

12. The system of claim 11, wherein the ablation geometry shaping module is configured to transmit the ablation pattern to an electrode connection multiplexer controller configured to supply electrical current to a selected one, or set of two or more, conductive wires in response to the ablation pattern.

* * * * *